(12) United States Patent
Garfield et al.

(10) Patent No.: US 10,449,183 B2
(45) Date of Patent: Oct. 22, 2019

(54) METHODS FOR INHIBITING PRETERM LABOR AND UTERINE CONTRACTILITY DISORDERS AND PREVENTING CERVICAL RIPENING

(71) Applicant: DIGNITY HEALTH, Phoenix, AZ (US)

(72) Inventors: Robert Garfield, Goodyear, AZ (US); Shao-Qing Shi, Goodyear, AZ (US); Leili Shi, Goodyear, AZ (US)

(73) Assignee: Dignity Health, Phoenix, AZ (US)

( * ) Notice: Subject to any disclaimer, the term of this patent is extended or adjusted under 35 U.S.C. 154(b) by 0 days.

(21) Appl. No.: 15/806,512

(22) Filed: Nov. 8, 2017

(65) Prior Publication Data

US 2018/0117024 A1  May 3, 2018

Related U.S. Application Data

(63) Continuation of application No. 13/605,767, filed on Sep. 6, 2012, now abandoned, which is a continuation-in-part of application No. PCT/US2011/027788, filed on Mar. 9, 2011.

(60) Provisional application No. 61/434,309, filed on Jan. 19, 2011, provisional application No. 61/311,944, filed on Mar. 9, 2010.

(51) Int. Cl.
| | | |
|---|---|---|
| *A61K 31/4422* | (2006.01) | |
| *A61K 31/57* | (2006.01) | |
| *A61K 31/405* | (2006.01) | |
| *A61K 9/00* | (2006.01) | |
| *A61K 47/44* | (2017.01) | |

(52) U.S. Cl.
CPC ........ *A61K 31/4422* (2013.01); *A61K 9/0014* (2013.01); *A61K 9/0019* (2013.01); *A61K 9/0034* (2013.01); *A61K 9/0043* (2013.01); *A61K 31/405* (2013.01); *A61K 31/57* (2013.01); *A61K 47/44* (2013.01)

(58) Field of Classification Search
CPC ........ A61K 31/57; A61K 47/12; A61K 47/14; A61K 47/44; A61K 9/0014; A61P 15/06
See application file for complete search history.

(56) References Cited

U.S. PATENT DOCUMENTS

| | | | | |
|---|---|---|---|---|
| 5,370,135 A | * | 12/1994 | Dullien | G01N 33/743 128/898 |
| 5,409,955 A | * | 4/1995 | Bockow | A61K 31/60 514/533 |
| 2004/0266025 A1 | * | 12/2004 | Hickok | A61K 31/20 436/518 |
| 2007/0071777 A1 | * | 3/2007 | Bromer | A61K 9/1075 424/400 |
| 2008/0188829 A1 | * | 8/2008 | Creasy | A61K 31/57 604/522 |

OTHER PUBLICATIONS

Lee et al (Natural Progesterone, published online 2006) (Year: 2006).*

Dodd et al (International Journal of Women's Health vol. 1, pp. 73-84, published 2009 (Year: 2009).*

* cited by examiner

*Primary Examiner* — Timothy P Thomas
*Assistant Examiner* — George W Kosturko
(74) *Attorney, Agent, or Firm* — Rodney J. Fuller; Booth Udall Fuller, PLC

(57) ABSTRACT

The invention relates to methods and pharmaceutical compositions for inhibiting or preventing preterm birth, inhibiting or delaying cervical ripening, inhibiting myometrial contractility and treating or inhibiting uterine contractility disorders. The methods comprise administering an effective amount of a composition comprising steroid hormones such as soluble progesterone.

13 Claims, 24 Drawing Sheets

(A)

(B)

Structures of embodiments on the invention

A. Progesterone (P4)

B. Promegestone (R5020)

C. 17-hydroxyprogesterone

D. 17-hydroxyprogesterone caproate

E. Nifedipine

F. Indomethacin

METHODS FOR INHIBITING PRETERM LABOR AND UTERINE CONTRACTILITY DISORDERS AND PREVENTING CERVICAL RIPENING

This application is a continuation of U.S. application Ser. No. 13/605,767, filed on Sep. 6, 2012 (published as 20130023505), which is a continuation-in-part of, and includes a claim of priority under 35 U.S.C. § 120 to, International Application No. PCT/US2011/027788, filed on Mar. 9, 2011, which designated the U.S. and that International Application was published under PCT Article 21(2) in English. This application also includes a claim of priority under 35 U.S.C. § 119(e) to U.S. Ser. No. 61/311,944 filed Mar. 9, 2010 and to U.S. Ser. No. 61/434,309 filed Jan. 19, 2011, the contents of all of which are hereby incorporated by reference in their entireties.

FIELD OF INVENTION

The invention relates to methods for inhibiting or preventing preterm birth, delaying cervical ripening, inhibiting myometrial contractility and treating uterine contractility disorders, in subjects in need thereof. The method comprises administering an effective amount of a steroid hormone such as progesterone or a pharmaceutical equivalent, analog, derivative or a salt thereof. The invention also relates to pharmaceutical compositions and kits, comprising steroid hormones such as progesterone or a pharmaceutical equivalent, analog, derivative or a salt thereof and a pharmaceutically acceptable carrier.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Preterm birth (less than 37 completed weeks of gestation) is one of the major problems and challenges in obstetrics. The frequency of preterm births is about 12-13% in the USA and 5-9% in many other developed countries. Despite all efforts to reduce the number of preterm births the problem is continuing to escalate. Since 1990 the percentage of births delivered preterm has risen more than 20 percent and is 36 percent higher since the early 1980s in the USA.[3] Preterm birth is not only a major determinant of neonatal and infant morbidity, including neurodevelopmental handicaps, chronic respiratory problems, intraventricular hemorrhage, infection, retrolental fibroplasia, and necrotizing enterocolitis, but it is also the single most important cause of perinatal mortality in North America, Europe and particularly in undeveloped countries. Additionally, the neonatal and long-term health care costs of preterm infants impose a considerable economic strain both on individual families and on healthcare costs (>$26.2 billion in 2005 in the USA).

Both uterine and cervical functions play important roles in the onset and progression of term and preterm labor and delivery. The cervix undergoes dramatic changes throughout pregnancy and parturition, a process that is termed cervical ripening—from a firm, rigid and closed state that is protecting the special milieu of the fetus from the environment, to a soft and easy-to-open state that is essential for successful vaginal delivery. The cervix is dominated by fibrous connective tissue that is composed of an extracellular matrix which consists mostly of collagen (70% type I and ~30% type III) with elastin and proteoglycans and a cellular portion that consists of smooth muscles, fibroblasts, epithelium and blood vessels. Cervical ripening is an active biochemical process, which occurs independent of uterine contractions. Studies have shown that cervical ripening is associated with a strong reorganization of the extracellular matrix, especially collagen: Not only does the concentration decrease by 30-70%, but there is also a switch from insoluble to more soluble collagen. Ripening of the cervix is an inflammatory-like reaction with infiltration of leukocytes, increase of cytokines (interleukin (IL)-1 and IL-8) and an increase in metalloproteinases. This process also seems to be at least partially regulated by steroid hormones (in particular progesterone (P4) and estrogen), as antiprogestins successfully induce cervical ripening. Other hormones and mediators shown to be involved in cervical ripening are dihydrotestosterone, prostaglandins, and local mediators such as platelet-activating factor and nitric oxide. Various methods have been used to evaluate cervical ripening and effects of progestins, including cervical length. However the biochemical mechanisms that are responsible for the remarkable changes in the cervix remain poorly understood. Although progesterone has been known to be used for recurrent or high risk preterm labor (PTL), its current use is crystalline progesterone in micronized form, and used to treat preterm labor and uterine contractile disorders by the often inconvenient and less effective routes of vaginal, oral or IM. Since the half life of progesterone is roughly 32 hours, progesterone by this matter must be given daily, and since crystalline progesterone can only be dissolved in oil, it can only be applied via vaginal administration or injected IM.

SUMMARY OF THE INVENTION

The invention provides methods for inhibiting preterm birth in a subject in need thereof. The methods comprise providing a composition comprising a steroid hormone (for example progesterone (P4) or a pharmaceutical equivalent, analog, derivative or a salt thereof) and administering a therapeutically effective amount of the composition to the subject to inhibit preterm birth, thereby inhibiting preterm birth.

The invention also provides methods for preventing preterm birth in a subject in need thereof. The methods comprise providing a composition comprising a steroid hormone (for example progesterone (P4) or a pharmaceutical equivalent, analog, derivative or a salt thereof) and administering a therapeutically effective amount of the composition to the subject to prevent preterm birth, thereby preventing preterm birth.

The invention further provides methods for inhibiting cervical ripening in a subject in need thereof. The method comprises providing a composition comprising a steroid hormone (for example progesterone (P4) or a pharmaceutical equivalent, analog, derivative or a salt thereof) and administering a therapeutically effective amount of the composition to the subject to inhibit cervical ripening, thereby inhibiting cervical ripening.

Methods for delaying cervical ripening in a subject in need thereof are also provided herein. The methods comprise providing a composition comprising a steroid hormone (for example progesterone (P4) or a pharmaceutical equivalent, analog, derivative or a salt thereof) and administering a therapeutically effective amount of the composition to the subject to delay cervical ripening, thereby delaying cervical ripening.

Further provided are methods for inhibiting myometrial contractility in a subject in need thereof. The methods comprise providing a composition comprising progesterone (P4) or a pharmaceutical equivalent, analog, derivative or a salt thereof and administering a therapeutically effective amount of the composition to the subject to inhibit myometrial contractility, thereby inhibiting myometrial contractility.

The invention also provides methods for treating uterine contractility disorders in a subject in need thereof. The methods comprise providing a composition comprising progesterone (P4) or a pharmaceutical equivalent, analog, derivative or a salt thereof and administering a therapeutically effective amount of the composition to the subject to treat uterine contractility disorders, thereby treating uterine contractility disorders.

The invention further provides methods for inhibiting uterine contractility disorders in a subject in need thereof. The method comprises providing a composition comprising progesterone (P4) or a pharmaceutical equivalent, analog, derivative or a salt thereof and administering a therapeutically effective amount of the composition to the subject to inhibit uterine contractility disorders, thereby inhibiting uterine contractility disorders.

The invention also provides that steroid hormones such as progesterone (P4) may be rendered soluble by mixing with agents such as cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution. The composition may be applied topically, intravenously, subcutaneously or nasally.

Also provided are pharmaceutical compositions and kits comprising steroid hormones (for example progesterone or a pharmaceutical equivalent, analog, derivative or a salt thereof) and a pharmaceutically acceptable carrier. The pharmaceutical compositions may be mixed with agents such as cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution, to render the steroid hormone soluble.

BRIEF DESCRIPTION OF THE FIGURES

Exemplary embodiments are illustrated in referenced figures. It is intended that the embodiments and figures disclosed herein are to be considered illustrative rather than restrictive.

FIG. 2A: Daily treatment with vehicle (controls) or P4 (4 mg, subcutaneously). Note that delivery is inhibited in the treatment group. FIG. 2B: Twice a day treatment with vehicle (controls) or vaginal P4 (15 mg bid). Note that no significant differences are observed at any time between controls vs. treated animals. FIG. 2C: Treatment daily with vehicle (controls) or 17P (10 mg, subcutaneously). Note that significant differences are only observed until day 19 of gestation. FIG. 2D: Twice a day treatment with vehicle (controls) or vaginal promegestone (R5020) (1 mg bid). Note that significant differences are observed only until day 19, but delivery is blocked in the treatment group. Asterisks indicate P<0.05 compared with controls.

FIG. 4A: Delivery times after daily treatment with vehicle (subcutaneously, controls), P4 (4 mg, subcutaneously) and 17P (10 mg, subcutaneously). Note that injections of P4 completely blocked delivery, whereas 17P had no significant effect on delaying term delivery (see also FIG. 5). FIG. 4B: Percent of animals delivering versus time of delivery following twice a day treatment with vaginal vehicle (controls), vaginal P4 (15 mg bid) and vaginal promegestone (R5020) (1 mg bid). Note that vaginal promegestone (R5020) completely blocked delivery, whereas vaginal P4 had no significant effect on delaying term delivery (P>0.05 compared with controls, see also FIG. 5).

DETAILED DESCRIPTION OF THE INVENTION

Figure 1:
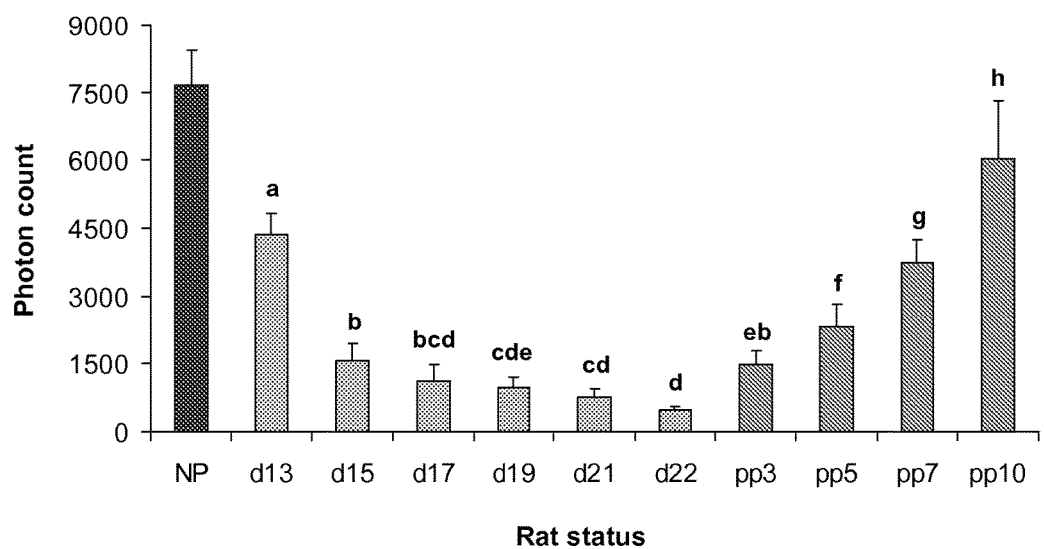
FIG. 1 depicts bar graphs showing means±SD of cervical light-induced fluorescence (LIF) obtained in vivo from nonpregnant (N=3), pregnant (d13, 15 and 17: N=12/group; d19 and d21: N=11/group; d22: N=6) and postpartum rats (pp3, 5 and 7: N=7; pp10: N=6). Significant differences (P<0.05) between groups are marked with different letters.

Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

As used herein, the term "P4" means progesterone.

As used herein, progesterone (P4) has the formula (Formula 1):

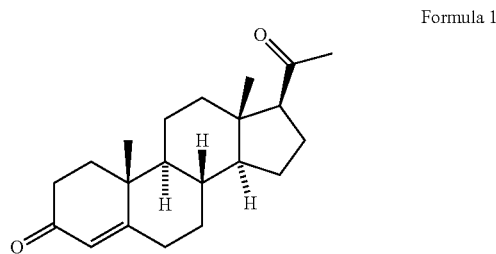

Formula 1

As used herein, Promegestone (R5020) has the formula (Formula 2):

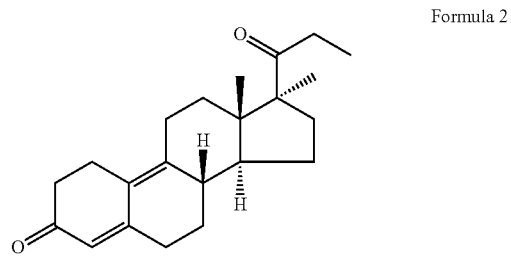

Formula 2

As used herein, 17-hydroxyprogesterone has the formula (Formula 3):

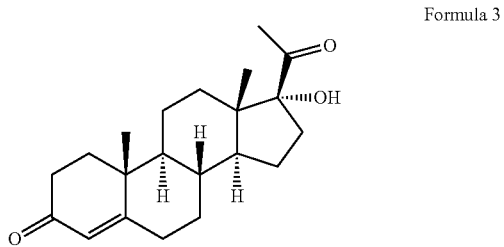

Formula 3

As used herein, 17-hydroxyprogesterone caproate has the formula (Formula 4):

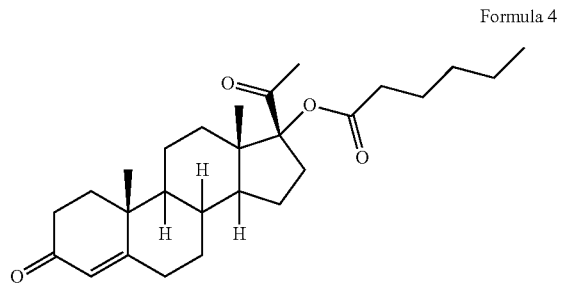

Formula 4

As used herein, Nifedipine has the formula (Formula 5):

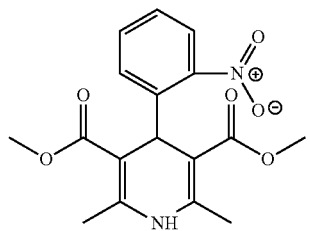

Formula 5

As used herein, Indomethacin has the formula (Formula 6):

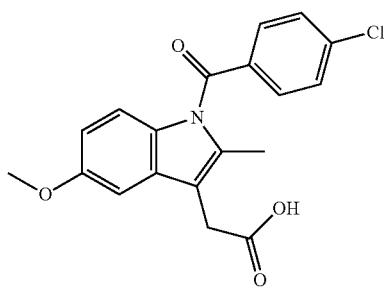

Formula 6

As used herein, the term "17P" means 17-alpha-hydroxy-progesterone caproate, a synthetic caproate ester of the naturally occurring metabolite of progesterone.

As used herein, the term "LIF" means light-induced fluorescence.

As used herein, soluble progesterone is progesterone (P4) mixed in or suspended in agents that render the progesterone soluble. Examples of such agents include but are not limited to cyclodextrins, sesame oil, fish oil, corn oil, olive oil, coconut oil, krill oil, omega fatty acids, mineral oil, peppermint oil, flaxseed oil, vitamin E oil, argan oil, saline solution, and/or glucose solution. For example, encapsulated progesterone (such as progesterone encapsulated in cyclodextrins) may be solubilized in any water based solutions including but not limited to saline solution or glucose solution to render it soluble. Alternately, powdered progesterone may be may be solubilized in any water based solutions including but not limited to saline solution or glucose solution to render it soluble. Additionally, crystalline or microcrystalline progesterone may be dissolved in various oils to render it soluble. Saline solution may be isotonic. Saline solution may be 0.9% w/v NaCl. Any form of progesterone (powdered, desiccated, crystalline or microcrystalline) may be dissolved with any suitable agent to render the progesterone soluble.

Therapeutic Methods of the Invention

The present invention is based, at least in part, on the findings described herein and thus the present invention describes methods, pharmaceutical compositions and kits for using steroid hormones to treat conditions in a subject, such as preterm birth. In an embodiment of the invention claimed herein, the steroid hormone is soluble. For example, the steroid hormone may be a progestogen or a pharmaceutical equivalent, analog, derivative or a salt thereof. In a preferred embodiment, the progestogen is progesterone (P4) and is mixed with or suspended in agents that render the progesterone soluble. These agents include but are not limited to cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution. In the most preferred embodiment, progesterone is mixed with fish oil, peppermint oil or isotonic saline solution. While not wishing to be bound by any particular theory, the inventors believe that the combination of progesterone and agents such as fish oil or peppermint oil, when administered topically (for example placed or rubbed on the abdominal surface of pregnant patients), delay the onset of contractions, labor and delivery. In an embodiment, delay of the delivery acts on the subject's myometrium, for instance, via inhibition of uterine contractility.

The present invention provides methods for inhibiting preterm birth or preventing preterm birth in a subject in need thereof. The method comprises providing a composition comprising a steroid hormone and administering a therapeutically effective amount of the composition to the subject to so as to inhibit preterm birth or prevent preterm birth. In an embodiment, the steroid hormone is soluble and is a progestogen (for example progesterone) or a pharmaceutical equivalent, analog, derivative or a salt thereof.

The invention also provides methods for delaying cervical ripening or inhibiting cervical ripening in subjects in need thereof. The methods comprise providing a composition comprising a steroid hormone and administering a therapeutically effective amount of the composition to the subject so as to delaying cervical ripening or inhibit cervical ripening. In an embodiment, the steroid hormone is soluble and is a progestogen (for example progesterone) or a pharmaceutical equivalent, analog, derivative or a salt thereof.

Also provided herein is a method for inhibiting myometrial contractility in a subject in need thereof. The method comprises providing a composition comprising progestogen (for example progesterone (P4) or a pharmaceutical equivalent, analog, derivative or a salt thereof) and administering a therapeutically effective amount of the composition to the subject to inhibit myometrial contractility. In one embodiment, the progestogen is soluble.

Further, the invention provides methods for treating uterine contractility disorders or inhibiting uterine contractility disorders in a subject in need thereof. The methods comprise providing a composition comprising progestogen (for example progesterone (P4) or a pharmaceutical equivalent, analog, derivative or a salt thereof) and administering a therapeutically effective amount of the composition to the subject to treat uterine contractility disorders or to inhibit uterine contractility disorders. In one embodiment, inhibiting uterine contractility disorders is promoting prophylaxis of uterine contractility disorders. In another embodiment, the progestogen is soluble.

In one embodiment, the present invention provides a method of suppressing delivery in a subject comprising administering a therapeutically effective amount of a composition comprising progestogen (for example, progesterone, or pharmaceutical equivalent, analog, derivative, or salt thereof) to the subject.

In some embodiments of the claimed methods, the steroid hormones are progestogens. In a further embodiment, progestogens include but are not limited to progesterone (P4) or a pharmaceutical equivalent, analog, derivative or a salt thereof, 17-hydroxyprogesterone or a pharmaceutical equivalent, analog, derivative or a salt thereof and progestins. In a preferred embodiment of the invention, the progestogen is progesterone (P4) or a pharmaceutical equivalent, analog, derivative or a salt thereof. In another embodiment of the invention, the progestins include but are not limited to 17-hydroxyprogesterone caproate or a pharmaceutical equivalent, analog, derivative or a salt thereof or promegestone (R5020) or a pharmaceutical equivalent, analog, derivative or a salt thereof. In a further embodiment of the instant invention, progestins include but are not limited to medroxyprogesterone acetate, norethindrone, norethindrone acetate, norethindrone enanthate, desogestrel, levonorgestrel, lynestrenol, ethynodiol diacetate, norgestrel, norgestimate, norethynodrel, gestodene, drospirenone, trimegstone, levodesogestrel, gestodyne, nesterone, etonogestrel and derivatives of 19-nor-testerone.

Since steroid hormones (such as progesterone (P4), 17-hydroxyprogesterone, 17-hydroxyprogesterone caproate, promegestone (R5020), or pharmaceutical equivalents, analogs, derivatives or salts thereof) have low solubilities, these hormones may be suspended in or mixed with agents that render the steroid hormones soluble. For instance, suspending or mixing steroid hormones with agents such as cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution, facilitates dissolution. In an embodiment, progesterone (P4) or pharmaceutical equivalents, analogs, derivatives or salts thereof may be suspended in or mixed with REPLENS vaginal moisturizer (available from Lil' Drug Store Products, Inc.).

In another embodiment, the steroid hormones may be mixed with carrier molecules such as cyclodextrins to render the steroid hormone (such as progesterone (P4)) soluble. Examples of cyclodextrins include but are not limited to α-cyclodextrin, β-cyclodextrin, γ-cyclodextrin, 2-hydroxypropyl-β-cyclodextrin and methyl-β-cyclodextrin. For example by encapsulating progesterone in cyclodextrins and solubilizing it in any of the agents described above, renders the progesterone soluble and can be used intravenously, topically, parenterally, nasally, subcutaneously, intravascularly, vaginally and/or topically or by other routes of administration.

In some preferred embodiments, progesterone (P4) or a pharmaceutical equivalent, analog, derivative or a salt thereof, is suspended in or mixed with omega fatty acid, omega-3-fatty acids, fish oil or peppermint oil and may be used topically, parenterally, nasally or by other routes of administration. In a preferred embodiment, administration of progesterone mixed with fish oil or peppermint oil is topical. For example, topical application of progesterone mixed in fish oil can inhibit delivery (such as preterm delivery) in a subject in need thereof.

In another preferred embodiment, progesterone (P4) is suspended in or mixed with saline solution (for example isotonic saline solution) to solubilize it and is subsequently administered via numerous routes of administration including but not limited to intravenous, topical, parenteral, nasal, subcutaneous injections, intravascular, vaginal and/or topical or by other routes of administration.

In another embodiment, the steroid hormone is 17-hydroxyprogesterone or a pharmaceutical equivalent, analog, derivative or a salt thereof and may be suspended in or mixed with agents such as cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution, to facilitate dissolution.

In a further embodiment, the steroid hormones are 17-hydroxyprogesterone caproate or a pharmaceutical equivalent, analog, derivative or a salt thereof and may be suspended in or mixed with agents such as cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution, facilitate dissolution.

In an additional embodiment, the steroid hormone is promegestone (R5020) or a pharmaceutical equivalent, analog, derivative or a salt thereof and may be suspended in or mixed agents such as cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution, to facilitate dissolution.

In an embodiment of the invention, the composition of the claimed methods comprises progesterone (P4) and further comprises nifedipine, indomethacin and/or oxytocin antagonists (for example atosiban). In one embodiment, progesterone (P4) and nifedipine may be administered concurrently. In another embodiment, progesterone (P4) and nifedipine may be administered sequentially. Similarly, in one embodiment, progesterone (P4) and indomethacin may be administered concurrently. In another embodiment, progesterone (P4) and indomethacin may be administered sequentially. Additionally, progesterone (P4) and oxytocin antagonists (for example atosiban) may be administered concurrently. In another embodiment, progesterone (P4) and oxytocin antagonists (for example atosiban) may be administered sequentially. In an additional embodiment, progesterone (P4), nifedipine and indomethacin may be administered concurrently. Alternatively, progesterone (P4), nifedipine and indomethacin may be administered sequentially.

In a preferred embodiment, progesterone (P4) is suspended in or mixed with agents that render progesterone soluble and is administered concurrently or sequentially with nifedipine and/or with indomethacin and/or with oxytocin antagonists such as atosiban. Examples of agents that render progesterone soluble include but are not limited to such as cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution.

In an embodiment, the composition comprising progesterone (with or without agents that render the progesterone soluble) and nifedipine and/or indomethacin is administered topically.

The subjects treated by the present invention include mammalian subjects, including but not limited to human, monkey, ape, dog, cat, cow, horse, goat, pig, rabbit, mouse and rat.

In a preferred embodiment, the subject is human. In an embodiment, the human subject is administered a steroid hormone (for example, progestogen such as progesterone (P4), 17-hydroxyprogesterone, 17-hydroxyprogesterone caproate, promegestone (R5020), or pharmaceutical equivalents, analogs, derivatives or a salts thereof) beginning at about the $16^{th}$ week up to the $37^{th}$ week of gestation, beginning at about $18^{th}$ week up to about $22^{nd}$ week of gestation, beginning at about $18^{th}$ week up to about $35^{th}$ week of gestation, beginning at about $18^{th}$ week up to about $37^{th}$ week of gestation, beginning at the time of positive pregnancy until the $37^{th}$ week of gestation or beginning at the time preterm labor is suspected up to when time of delivery is imminent. In an embodiment, the steroid hormone (such as progesterone (P4), 17-hydroxyprogesterone, 17-hydroxyprogesterone caproate, promegestone (R5020), or pharmaceutical equivalents, analogs, derivatives or salts thereof) is mixed with or suspended in agents to render the steroid hormones soluble and is applied topically. In some preferred embodiments, progesterone (P4) is mixed with fish oil, peppermint oil or with omega fatty acids and is applied topically, for example, by placing or rubbing the progesterone mixed in oil on the abdominal surface of a pregnant woman. In other preferred embodiments, the steroid hormones such as progesterone (P4) is mixed with saline solution (such as isotonic saline solution) and is administered intravenously, topically, nasally or via any other route of administration.

In another embodiment, the human subject is administered a steroid hormone (for example, progestogen such as progesterone (P4), 17-hydroxyprogesterone, 17-hydroxyprogesterone caproate, promegestone (R5020), or pharmaceutical equivalents, analogs, derivatives or a salts thereof) for about 2 to 4 weeks, for about 4 to 6 weeks, for about 6 to 8 weeks, for about 8 to 10 weeks, for about 10 to 12 weeks, for about 12 to 14 weeks, for about 14 to 19 weeks, for about 20 weeks, for about 21 weeks, for about 22 weeks, for about 23 weeks, for about 25 weeks, for about 26 weeks, for about 27 weeks, for about 28 weeks or for about 29 weeks, for about 30 weeks, for about 35 weeks or for about 37 weeks. In an embodiment, the steroid hormone (such as progesterone (P4), 17-hydroxyprogesterone, 17-hydroxyprogesterone caproate, promegestone (R5020), or pharmaceutical equivalents, analogs, derivatives or salts thereof) is mixed with or suspended in agents to render the steroid hormones soluble and is applied topically. In some preferred embodiments, progesterone (P4) is mixed with fish oil, peppermint oil or with omega fatty acids and is applied topically, for example, by placing or rubbing the progesterone mixed in oil on the abdominal surface of a pregnant woman. In other preferred embodiments, the steroid hormones such as progesterone (P4) is mixed with saline solution (such as isotonic saline solution) and is administered intravenously, topically, nasally or via any other route of administration.

In a further embodiment, the human subject is administered a steroid hormone (for example, progestogen such as progesterone (P4), 17-hydroxyprogesterone, 17-hydroxyprogesterone caproate, promegestone (R5020), or pharmaceutical equivalents, analogs, derivatives or salts thereof) when the pregnant woman's cervix length is greater than 1.0 cm, or when the cervix length is less than or equal to about 3.0 cm, or when the cervix length is between 1.0 and 8.0 cm. In an embodiment, the steroid hormone (such as progesterone (P4), 17-hydroxyprogesterone, 17-hydroxyprogesterone caproate, promegestone (R5020), or pharmaceutical equivalents, analogs, derivatives or salts thereof) is mixed with or suspended in agents to render the steroid hormones soluble and is applied topically. In some preferred embodiments, progesterone (P4) is mixed with fish oil or with omega fatty acids or with cyclodextrins and is applied topically, for example, by placing or rubbing the progesterone mixed in oil on the abdominal surface of a pregnant woman. In other preferred embodiments, the steroid hormones such as progesterone (P4) is mixed with saline solution (such as isotonic saline solution) and is administered intravenously, topically, nasally or via any other route of administration.

In one embodiment, the steroid hormones in the composition of the claimed methods (for example, progestogens such as progesterone (P4), 17-hydroxyprogesterone, 17-hydroxyprogesterone caproate, promegestone (R5020), or pharmaceutical equivalents, analogs, derivatives or a salts thereof) are in a soluble form, crystalline form, gel form, tablet form or encapsulated form.

Various methods may be utilized to administer the compositions comprising steroid hormones of the claimed methods, including but not limited to aerosol, nasal, oral, subcutaneous, transmucosal, transdermal, parenteral, implantable pump, continuous infusion, topical application, capsules, injections, intradermally, intravenously, intramuscularly, intraperitonealy, rectally, non-vaginally and/or vaginally. In a preferred embodiment of the claimed invention, the steroid hormone (for example progesterone (P4)) is administered topically or subcutaneously. In another preferred embodiment of the claimed methods, promegestone (R5020) is administered vaginally. In another preferred embodiment, progesterone (P4) is mixed with or suspended in agents to render it soluble and is applied topically by placing or rubbing on the abdominal surface of pregnant patients. Agents that render the steroid hormones soluble include but are not limited to cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution. In the most preferred embodiment of the claimed invention, progesterone is mixed with fish oil or peppermint oil and is applied topically to prevent or inhibit preterm birth and/or delay or inhibit cervical ripening. In other preferred embodiments, the steroid hormones such as progesterone (P4) is mixed with saline solution (such as isotonic saline solution) and is administered intravenously, topically, nasally or via any other route of administration so as to prevent or inhibit preterm birth and/or delay or inhibit cervical ripening In one embodiment, the present invention provides a method increasing bioavailability of a therapeutically effective composition. In one embodiment, increased bioavailability is shown by higher plasma levels of the composition. In another embodiment, the therapeutically effective composition includes progestogen (for example, progesterone, or pharmaceutical equivalent, analog, derivative, or salt thereof) to the subject. In another embodiment, the method includes topical delivery. In another embodiment, the method includes topical delivery in a single treatment.

Dosages of the Invention

In some embodiments of the invention, the effective amounts of the steroid hormone (for example progesterone (P4), 17-hydroxyprogesterone, 17-hydroxyprogesterone caproate, promegestone (R5020)) is about 0.5-1 mg/day, 1-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day, 2900-3000 mg/day, 3000-3100 mg/day, 3100-3200 mg/day, 3200-3300 mg/day, 3300-3400 mg/day, 3400-3500 mg/day, 3500-3600 mg/day, 3600-3700 mg/day, 3700-3800 mg/day, 3800-3900 mg/day, 3900-4000 mg/day, 4000-4200 mg/day, 4200-4400 mg/day, 4400-4600 mg/day, 4600-4800 mg/day or 4800-5000 mg/day. In one embodiment, the steroid hormone administered at the aforementioned dosage is progesterone (P4) or a pharmaceutical equivalent, analog, derivative or a salt thereof. In another embodiment, the steroid hormone administered at the aforementioned dosage is 17-hydroxyprogesterone caproate or a pharmaceutical equivalent, analog, derivative or a salt thereof. In a further embodiment, the steroid embodiment administered at the aforementioned dosage is promegestone (R5020) or a pharmaceutical equivalent, analog, derivative or a salt thereof. In an embodiment, the steroid hormone, for example progesterone (P4) such as soluble progesterone (P4) or a pharmaceutical equivalent, analog, derivative or a salt thereof is administered daily, biweekly, weekly, every fortnight or monthly. In a preferred embodiment, progesterone (P4) such as soluble progesterone (P4) or a pharmaceutical equivalent, analog, derivative or a salt thereof is administered daily.

As described above, in one embodiment of the invention the steroid hormones including but not limited to progesterone (P4), 17-hydroxyprogesterone caproate, promegestone (R5020), or pharmaceutical equivalents, analogs, derivatives or a salts thereof, may be suspended in or mixed with agents that render the steroid hormone soluble. Such agents include but are not limited to cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution. The effective amount of the agent may be about 0.05-0.1 ml/mg of steroid hormone, 0.1-0.2 ml/mg of steroid hormone, 0.2-0.3 ml/mg of steroid hormone, 0.3-0.4 ml/mg of steroid hormone, 0.4-0.5 ml/mg of steroid hormone, 0.5-0.6 ml/mg of steroid hormone, 0.6-0.7 ml/mg of steroid hormone, 0.7-0.8 ml/mg of steroid hormone, 0.8-0.9 ml/mg of steroid hormone, 0.9-1.0 ml/mg of steroid hormone, 1.0-5.0 ml/mg of steroid hormone, 5.0-10.0 ml/mg of steroid hormone, 10.0-15.0 ml/mg of steroid hormone, 15.0-20.0 ml/mg of steroid hormone, 20.0-25.0 ml/mg of steroid hormone or 25.0-30.0 ml/mg of steroid hormone. In a preferred embodiment, progesterone (P4) is mixed with fish oil or peppermint oil or with saline solution wherein the aforementioned amounts are the effective amounts of the fish oil or peppermint oil or saline solution.

Further, the steroid hormones including but not limited to progesterone (P4), 17-hydroxyprogesterone caproate, promegestone (R5020), or pharmaceutical equivalents, analogs, derivatives or a salts thereof, may be administered concurrently or sequentially with an effective amount of Nifedipine. In some embodiments of the invention, the effective amounts of Nifedipine is about 0.5-1 mg/day, 1-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day, 2900-3000 mg/day, 3000-3100 mg/day, 3100-3200 mg/day, 3200-3300 mg/day, 3300-3400 mg/day, 3400-3500 mg/day, 3500-3600 mg/day, 3600-3700 mg/day, 3700-3800 mg/day, 3800-3900 mg/day, 3900-4000 mg/day, 4000-4200 mg/day, 4200-4400 mg/day, 4400-4600 mg/day, 4600-4800 mg/day or 4800-5000 mg/day.

In another embodiment of the invention, the steroid hormones including but not limited to progesterone (P4), 17-hydroxyprogesterone caproate, promegestone (R5020), or pharmaceutical equivalents, analogs, derivatives or a salts thereof, may be administered concurrently or sequentially with an effective amount of Indomethacine. In some embodiments of the invention, the effective amounts of Indomethacin is about 0.5-1 mg/day, 1-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day, 2900-3000 mg/day, 3000-3100 mg/day, 3100-3200 mg/day, 3200-3300 mg/day, 3300-3400 mg/day, 3400-3500 mg/day, 3500-3600 mg/day, 3600-3700 mg/day, 3700-3800 mg/day, 3800-3900 mg/day, 3900-4000 mg/day, 4000-4200 mg/day, 4200-4400 mg/day, 4400-4600 mg/day, 4600-4800 mg/day or 4800-5000 mg/day.

Typical dosages of an effective amount of a steroid hormone, progesterone (P4), 17-hydroxyprogesterone, 17-hydroxyprogesterone caproate, promegestone (R5020), or pharmaceutical equivalents, analogs, derivatives or a salts thereof, can be in the ranges recommended by the manufacturer where known therapeutic compounds are used, and also as indicated to the skilled artisan by the in vitro responses or responses in animal models. The same or similar dosing can be used in accordance with various embodiments of the present invention, or an alternate dosage may be used in connection with alternate embodiments of the invention, with or without oil, nifedipine or indomethacin. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

Pharmaceutical Compositions

The instant invention also provides a pharmaceutical composition comprising a steroid hormone such as progesterone (P4), 17-hydroxyprogesterone, 17-hydroxyprogesterone caproate, promegestone (R5020), or pharmaceutical equivalents, analogs, derivatives or salts thereof and a pharmaceutically acceptable carrier. In one embodiment, the pharmaceutical composition further comprises agents that render the steroid hormone soluble. Such agents include but are not limited to cyclodextrins, sesame oil, fish oil, corn oil, olive oil, coconut oil, krill oil, omega fatty acids, mineral oil, peppermint oil, flaxseed oil, vitamin E oil, argan oil and/or glucose solution. In another embodiment, the pharmaceutical composition further comprises Nifedipine. In yet another embodiment, the pharmaceutical composition further comprises Indomethacin. In a further embodiment, the pharmaceutical composition further comprises a steroid hormone, Nifedipine and Indomethacin.

In one embodiment, the effective amount of the agent in the pharmaceutical composition of about 0.05-0.1 ml/mg of steroid hormone, 0.1-0.2 ml/mg of steroid hormone, 0.2-0.3 ml/mg of steroid hormone, 0.3-0.4 ml/mg of steroid hormone, 0.4-0.5 ml/mg of steroid hormone, 0.5-0.6 ml/mg of steroid hormone, 0.6-0.7 ml/mg of steroid hormone, 0.7-0.8 ml/mg of steroid hormone, 0.8-0.9 ml/mg of steroid hormone, 0.9-1.0 ml/mg of steroid hormone, 1.0-5.0 ml/mg of steroid hormone, 5.0-10.0 ml/mg of steroid hormone, 10.0-15.0 ml/mg of steroid hormone, 15.0-20.0 ml/mg of steroid hormone, 20.0-25.0 ml/mg of steroid hormone or 25.0-30.0 ml/mg of steroid hormone.

In an embodiment, the therapeutically effective amount of the steroid hormone (such as) in the pharmaceutical composition is about 0.5-1 mg/day, 1-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day, 95-100 mg/day, 100-200 mg/day, 200-300 mg/day, 300-500 mg/day, 500-700 mg/day, 700-1000 mg/day, 1000-2000 mg/day, 2000-3000 mg/day, 3000-4000 mg/day or 4000-5000 mg/day.

In an additional embodiment, the effective amount of indomethacin in the pharmaceutical composition is about 0.5-1 mg/day, 1-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day.

In another embodiment, effective amount of nifedipine in the pharmaceutical composition is about 0.5-1 mg/day, 1-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day.

In various embodiments, the present invention provides pharmaceutical compositions including a pharmaceutically acceptable excipient along with a therapeutically effective amount of a steroid hormone, such as progesterone (P4), 17-hydroxyprogesterone, 17-hydroxyprogesterone caproate, promegestone (R5020), or pharmaceutical equivalents, analogs, derivatives or salts thereof "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly per os (p.o., by mouth) or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Kits of the Invention

The present invention is also directed to a kit to treat and/or inhibit preterm delivery. The kit is an assemblage of materials or components, including at least one of the inventive compositions. Thus, in some embodiments the kit contains a composition including progesterone or pharmaceutical equivalent, analog, derivative, or salt thereof for topical application, as described above.

In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to apply progesterone topically. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Advantages of the Invention

As described herein, use of steroid hormones like progesterone (P4), when mixed with agents that render the steroid hormone soluble, inhibit uterine contractility and cervical ripening, prevent preterm labor and prevent miscarriages. Agents that render steroid hormones soluble include but are not limited to cyclodextrins, sesame oil, fish oil, corn oil, olive oil, coconut oil, krill oil, omega fatty acids, mineral oil, peppermint oil, flaxseed oil, vitamin E oil, argan oil, saline solution and/or glucose solution. Progesterone has a relatively short half life of about 30 minutes and therefore must be administered daily. Progesterone dissolved in saline solution (for example isotonic saline solution) or in glucose solution may be administered by subcutaneous injections, intravascularly (IV), vaginally, topically or by other routes not applicable for oily compositions of progesterone. Oily compositions of progesterone such as those dissolved in fish oil, omega fatty acid or peppermint oil may readily be used topically, vaginally, intramuscularly or via other routes of administration.

In non-pregnant women, progesterone (P4) when mixed with the aforementioned agents is useful for postmenopausal hormone replacement therapy with and without estrogen, prevention of amenorrhea and abnormal uterine bleeding due to hormonal imbalance and prevention of cancer fibroids. Soluble progesterone is particularly useful because it can be used in injections, intravenously, subcutaneously, parenterally, topically and/or nasally.

EXAMPLES

The following example is provided to better illustrate the claimed invention and is not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

As disclosed herein, the inventor evaluated cervical changes and delivery at term during pregnancy in rats after various progestin treatments. Pregnant rats were treated by various routes and vehicles with progesterone (P4), 17-alpha-hydroxyprogesterone caproate (17P), promegestone (R5020) and RU-486. Delivery time was determined and cervical ripening assessed in vivo by collagen light-induced fluorescence (LIF).

As further disclosed herein, the cervix is rigid in P4 injection, 17P and vaginal promegestone (R5020) groups versus controls. Vaginal P4 had no effect. RU-486 treatment softened the cervix during preterm delivery. Only subcutaneously P4, promegestone (R5020) (subcutaneously and vaginal) and topical P4 in sesame and fish oil inhibits delivery. Delivery was not changed by subcutaneously 17P, vaginal P4, oral P4 and topical P4 in Replens. These results demonstrate why many of the commonly used treatments for preterm labor are not efficacious.

Example 1

Experimental Methods
Animals

Nonpregnant and timed-pregnant Sprague-Dawley rats (200-250 g) from Charles-River Laboratories (Wilmington, Mass., USA) were delivered to animal care facilities on day 12 of gestation (day 1 being the day when a sperm plug was observed). The animals were housed separately, with free access to food and water and maintained on a constant 12-hour light-dark cycle. Control pregnant rats were spontaneously delivering on day 22 and 23 of gestation. For the measurements with the collascope the animals were anaesthetized (interperitoneal (i.p). injection) with a combination of xylazine (Gemini, Burns Veterinary Supply Inc, Rockville Center, N.Y., USA) and ketamine HCl (Ketaset; Fort Dodge Laboratories Inc, Fort Dodge, Iowa, USA). The animals were randomly allocated to one of the groups and sacrificed by carbon dioxide inhalation on day 3, 5, 7 and 10 postpartum or on day 25 of pregnancy in the groups with delayed delivery. All procedures were approved by the Animal Care and Use Committee of the St. Joseph's Hospital and Medical Center in Phoenix.

Treatments

Prior to any treatment LIF measurements were made in control rats throughout pregnancy and postpartum to estimate the LIF profile during gestation (see FIG. 1). Pregnant rats (N=6/group) were treated (see FIG. 2), when not otherwise mentioned (see FIG. 3), from day 13 of pregnancy until delivery. Single daily treatments were performed at 8 a.m. and twice a day treatments at 8 a.m. and 8 p.m. All single injections (4 mg P4, 10 mg 17P, 2 mg promegestone (R5020)) were by the subcutaneous route (s.c.) in sesame oil (0.2 ml), which was also used for the controls. Vaginal gels were applied twice a day with a blunt ball-top needle deep into the vagina. Crinone was used for the P4 vaginal group (equivalent volumes of Crinone were used for 2-15 mg P4/treatment), all data presented show the results of the highest dose (total daily dose of 30 mg P4=⅓ of a applicator of 8% Crinone that contains 90 mg P4). For the vaginal promegestone (R5020) group micronized promegestone (R5020) (1 mg/treatment) was mixed into 0.18 ml of Replens. The control rats for the vaginal groups were treated with Replens (0.18 ml/treatment). For oral P4 treatments (15 mg, bid, vehicle sesame oil or $H_2O$, volume 1 ml) gavage was used. For topical P4 treatment (15 mg, bid, P4 in 1 ml sesame oil, fish oil or in Replens) the drug was applied on the back of animals that were shaved on day 13, 17 and 21. In some animals (N=6) RU-486 (3 mg in 0.2 ml sesame oil) was injected subcutaneously once on day 16 of gestation.

Reagents

Crystalline progesterone (used for oral, topical and subcutaneous P4), RU-486, sesame oil and ethanol were purchased from Sigma (St Louis, Mo., USA), fish oil (concentrated omega-3 fatty acids) was obtained from General Nutrition Corp. (Pittsburgh, Pa., USA), 17-alpha-hydroxy-progesterone caproate from MP Biomedicals (Solon, Ohio, USA), promegestone (promegestone (R5020)) from Roussel Uclaf, France. P4, 17P, promegestone (R5020) and RU-486 were dissolved in ethanol and then mixed with sesame oil. Crinone (micronized P4 in Replens, a bioadhesive gel) was used for vaginal P4) and Replens were gifts from Columbia Laboratories (Livingston, N.J., USA).

Assessment of Cervical Ripening

The amount of cervical collagen was evaluated in vivo (only in group subcutaneously P4, vaginal P4, subcutaneously 17P, vaginal promegestone (R5020), subcutaneously RU-486) by measurement of the auto-fluorescent properties of cross-linked collagen with a new prototype of an instrument, termed collascope (Reproductive Research Technologies, Houston, Tex., USA), as used previously with an earlier prototype.

After insertion of a small speculum into the vagina of the anesthetized animal, the optical probe of the collascope was placed on the surface of the exocervix. The probe, which is connected to the main unit of the instrument by a fiberoptic cable, delivers not only excitation light (wavelength: 339 nm) onto the cervix but also carries the fluorescent light (mainly caused by pyridinoline cross-links of collagen with a maximum peak at 390 nm) back to the instrument to a CCD camera to display the full spectrum of fluorescence and analysis of the photons emitted by the cervix. The exposure time for excitation was 100 msec. The average of 20 measurements of the detected fluorescent intensity (photon count) at 390 nm was used for each animal at any given time. Measurements of cervical light-induced fluorescence (LIF) were performed on nonpregnant animals once and in pregnant animals every other day starting at day 13 of gestation until delivery and on postpartum day 3 and/or postpartum day 5 (see FIGS. 2 and 3), and for some animals also on postpartum days 7 and 10 (see FIGS. 1 and 3).

Determining the Changes in Delivery Time

Figure 4:
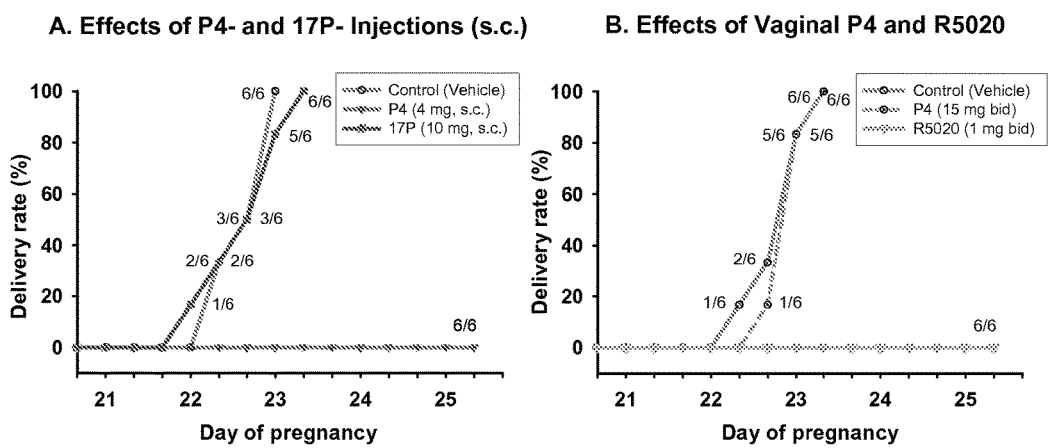
FIG. 4 depicts the percent of animals delivering versus day of pregnancy after various treatments.
Figure 5:
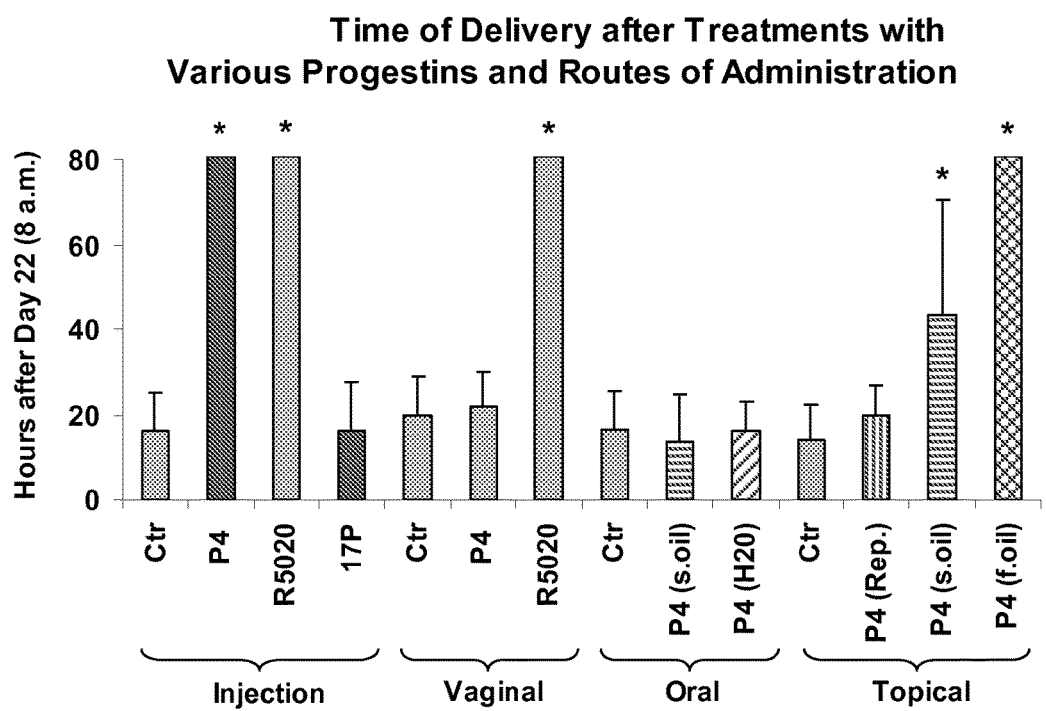
FIG. 5 depicts the time of delivery (=hours after 8 a.m. of day 22 of gestation) of pregnant rats treated with vehicles (controls) and various progestins by different routes of administration—injections (subcutaneously; daily): vehicle: sesame oil; P4 (4 mg); 17P (10 mg); vaginal (bid): vehicle: Replens; P4 (15 mg, Crinone); promegestone (R5020) (1 mg); oral (bid): vehicle: sesame oil or $H_2O$; P4 (15 mg); topical (bid): vehicle: Replens, sesame oil or fish oil; P4 (15 mg). Rats with delayed parturition were sacrificed on day 25. Asterisks indicate P<0.05 compared with controls.

Times of delivery (see also FIG. 4) of controls and various treatment groups were determined as hours after 8 a.m. of day 22 of gestation (FIG. 5). The expulsion of one pup was defined as delivery.

Statistical Analyses

Figure 2:
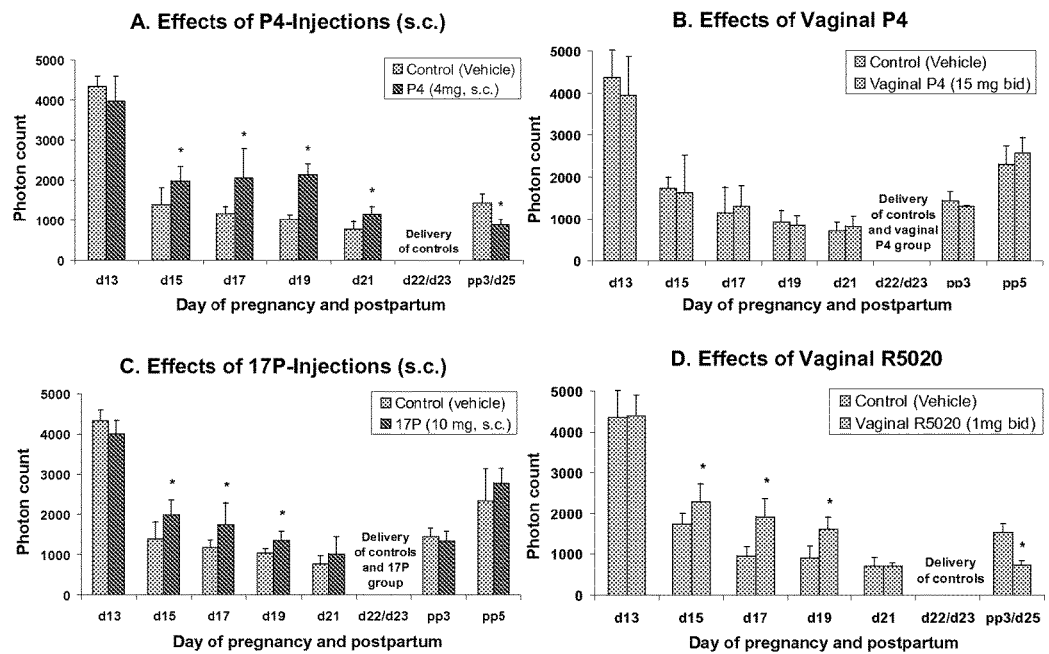
FIG. 2 depicts bar graphs showing means±SD of cervical light-induced fluorescence (LIF) obtained in vivo from pregnant rats at different days of pregnancy and postpartum (N=6/group) treated with various progestins or vehicle.
Figure 3:
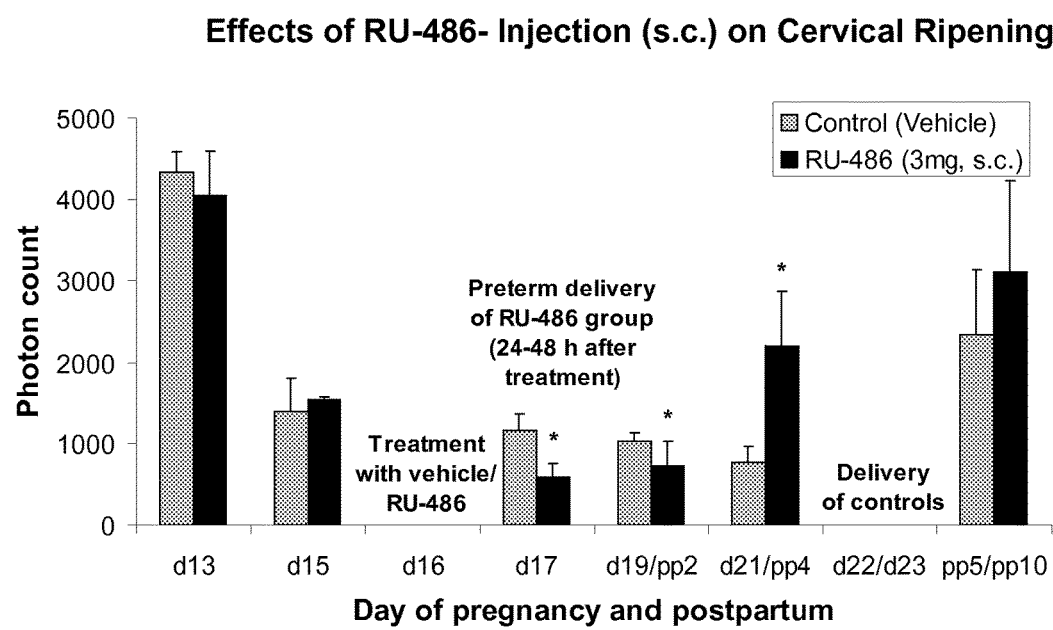
FIG. 3 depicts bar graphs showing means±SD of cervical light-induced fluorescence (LIF) obtained in vivo from pregnant rats at different days of pregnancy and postpartum (N=6/group) treated once on day 16 with vehicle (controls) or RU-486 (3 mg subcutaneously). Asterisks indicate $P<0.05$ compared with controls.

The cervical LIFs obtained at different times of gestation (FIG. 1) were compared using one-way analysis of variance (ANOVA) and multiple pairwise comparison procedures (Holm-Sidak). Student's t-test was used to compare the LIF results of a treatment group to its specific control group at any time in gestation and postpartum and also to determine the differences in delivery times (FIGS. 2, 3 and 5). A two-tailed probability value of $P<0.05$ was considered statistically significant.

Example 2

Effects on Preterm Delivery

LIF in Nonpregnant, Pregnant and Postpartum Rats:

Measurements of cervical light-induced-fluorescence (LIF) in pregnant, non-treated animals show (FIG. 1) a continuously decreasing photon count throughout pregnancy, reaching lowest values at term, and reversal postpartum. After significant ($P<0.05$) decrease from day 13 to day 15 LIF reaches a wider plateau of non-significant ($P>0.05$) decreases prior to delivery. LIF values progressively increase postpartum ($P<0.05$).

Effects of Injections of P4 on LIF:

LIF is significantly ($P<0.05$) higher in the P4 injection group compared with vehicle controls for any day of gestation (FIG. 2A). There is no difference ($P<0.05$) between day 25 (delayed delivery) in the P4 injection group (and delivery is blocked see FIG. 4A) compared to control animals at day 21 of gestation. LIF before treatment at day 13 shows no significant differences ($P>0.05$) between the treatment and the control group and this is similar for all treatment groups mentioned with other treatments (FIGS. 2A-D and 3).

Effects of Vaginal P4 on LIF:

There are no significant differences ($P>0.05$) between the vaginal P4 group and vehicle controls at any time in gestation (FIG. 2B) and vaginal P4 failed to inhibit delivery (see FIG. 4B).

Effects of Injections of 17P on LIF:

LIF is significantly higher ($P<0.05$) in the 17P treated group (until day 19 only) compared with vehicle controls (FIG. 2C).

Effects of Vaginal Promegestone (R5020) on LIF:

LIF is significantly higher ($P<0.05$) in the promegestone (R5020) treated group (until day 19 only) compared with vehicle controls (FIG. 2D).

Effects of a Single Injection of RU-486 on LIF:

LIF is significantly lower ($P<0.05$) in the RU-486 treated group 24 and 72 hours after treatment compared with vehicle controls (FIG. 3). LIF is higher in the RU-486 treated group 5 days after treatment compared with vehicle controls ($P<0.05$).

Effects of Injections of P4 and 17P on Time of Delivery:

Injections of P4, but not 17P, completely block delivery (FIG. 4A).

Effects of Vaginal P4 and Promegestone (R5020) on Time of Delivery:

Vaginal promegestone (R5020), but not vaginal P4, completely block delivery (FIG. 4B).

Effect of Various Progestins and Routes of Administration on Time of Delivery:

FIG. 5 summarizes the results of the different treatment groups on time of delivery and shows additional treatment groups. Animals treated as mentioned above. Other treatment groups followed the same design with treatments starting at day 13 of gestation until delivery. Additional treatment groups: Injections of promegestone (R5020) also completely block delivery. Oral P4 suspended in sesame oil or $H_2O$ had no effect on time of delivery. However, topical P4 in sesame oil (partially) and in fish oil (completely), but not in Replens prolongs delivery ($P<0.05$).

Effects of RU-486 on Time of Delivery:

The P4 antagonist RU-486 (mifepristone) induced preterm delivery 24-48 hours after injection (see FIG. 3; 4 of 6 animals delivered after 24 hours and the remaining two animals delivered within 48 hours after treatment).

Example 3

Applications of Progesterone

Various studies have raised questions about the ability of P4 and 17P to inhibit recurrent preterm labor and whether these progestins have effects on the cervix to prevent cervical ripening. It is not established which of the progestins and which route of administration is superior and there is controversy in the findings. Existing treatment do not completely prevent preterm birth and in many studies, women were exposed to progestins whether they needed it or not.

As described herein, injections of P4 show (FIG. 2A) the longest effect on delaying cervical ripening in rats of all compounds used. This treatment inhibited the progression of softening of the cervix in a stage of rat pregnancy, where the physiological P4-levels are still rising.[33,34] Thus, higher P4 levels in midgestation of pregnancy in rat has an anti-ripening effect on the cervix. Exogenous P4, administered by subcutaneous injections also decelerate the consequences of the sharp withdrawal of P4 that occurs at day 19 of rat pregnancy.[33,34] The consequences of blocking the P4 receptors during pregnancy with the P4 antagonist RU-486 results in termination of pregnancy in both rats and humans.[28,35] RU-486-induced cervical ripening occurs after 24 hours followed by preterm delivery (FIG. 3) and this confirms effects of antiprogestins on the cervix[36] and indicates the importance of P4 in control of the cervix and maintaining pregnancy.

Data described herein demonstrates that the intrinsic properties of the progestins dictate their affects on the cervix and myometrium. Thus, 17P and promegestone (R5020) delayed cervical ripening but not at term immediately preceding delivery and subcutaneous and vaginal promegestone (R5020) and parenteral P4 prevented delivery. Cervical ripening is only attenuated until day 19 of gestation with promegestone (R5020) and 17P in contrast to injection of P4 which also prevents further ripening on day 21 (FIG. 2A, 2C, 2D). This indicates that P4 accomplishes inhibitory effects on the cervix beyond the ability of promegestone (R5020) and 17P and demonstrates how properties of the progestins are significant factors affecting action.

Despite any of the treatments with progestins the cervix still manages to ripen at the end of pregnancy (FIGS. 2A-D). The fact that prophylactic parenteral P4 can only delay, but not completely inhibit cervical ripening indicates the involvement of other control pathways in the ripening process. Following the concept of the liver first-pass effect after administration of oral drugs, de Ziegler et al. established the term "uterine first-pass effect" to point out the minimized systemic, but optimized uterine exposure after transvaginal treatment with sex steroids. However, in data described herein for vaginal P4, even at a very high dose (7.5× the injected dose) had no effect on cervical ripening and on delivery The importance of the vehicle is demonstrated by the observations where topical P4 in fish oil completely, in sesame oil only partially and in Replens not at all inhibits delivery (FIG. 5). This indicates that Replens may not release P4 as effectively as oil. It could be suggested that P4 regulates parturition through genomic actions via various proteins that are thought to be involved in controlling myometrial contractility.

Recently, it was shown that P4, at concentrations equivalent to those present in the placenta and uterus, inhibits spontaneous myometrial contractility by nongenomic mechanism.[39] As disclosed herein, the inventors measured delivery and cervical ripening. Delivery at term or preterm is thought from many studies to be due to these two main processes and involves both uterine muscle activity and changes in the cervical connective tissue. The inventor demonstrates that delivery is completely inhibited by some progestin treatments (e.g. subcutaneous P4 and both subcutaneous and vaginal promegestone (R5020)), but cervical ripening is delayed but not entirely blocked during the final days of gestation (e.g. subcutaneous P4) or not significantly different from controls (e.g. vaginal promegestone (R5020))

on day 21. Therefore inhibition of delivery is not due to an unripe cervix, but must be due to inhibition of uterine contractions. On the other hand 17P partly delays ripening, similar to subcutaneous P4, and is not significantly different from controls at day 21, like promegestone (R5020), but does not block delivery at all. RU-486, the antiprogestin used in this study is well known to act both on the cervix and uterus to induce delivery by stimulation of uterine contractility and cervical ripening. Additionally the uterine contractility increases dramatically during spontaneous delivery at term and preterm after RU-486 treatment. 17P had no effect on delaying term delivery supporting the conclusion that 17P is not an effective treatment for preventing birth.

In addition use of progestins for other indications (such as menstrual cramps, uterine and other cancers, osteoporosis, contraception, to oppose unwanted effects of estrogens, amenorrhea and abnormal uterine bleeding, infertility, endometriosis, etc.) could be greatly improved by the methods described herein.

Example 4

Figure 9:
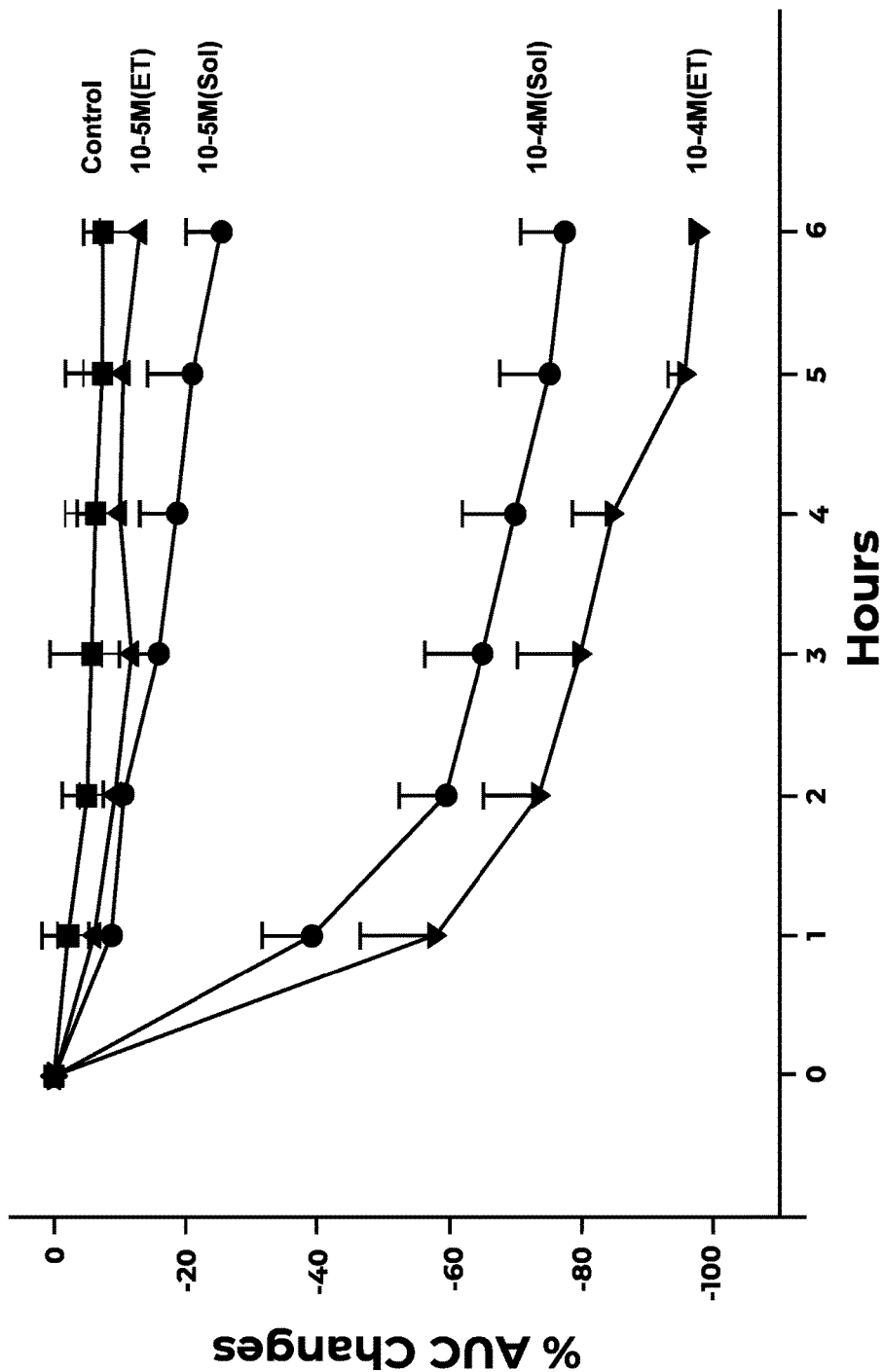
FIG. 9 depicts, in accordance with an embodiment herein, effects of soluble (SOL) progesterone and crystalline P4 in ethanol (ET) on myometrial contractility.
Figure 10:
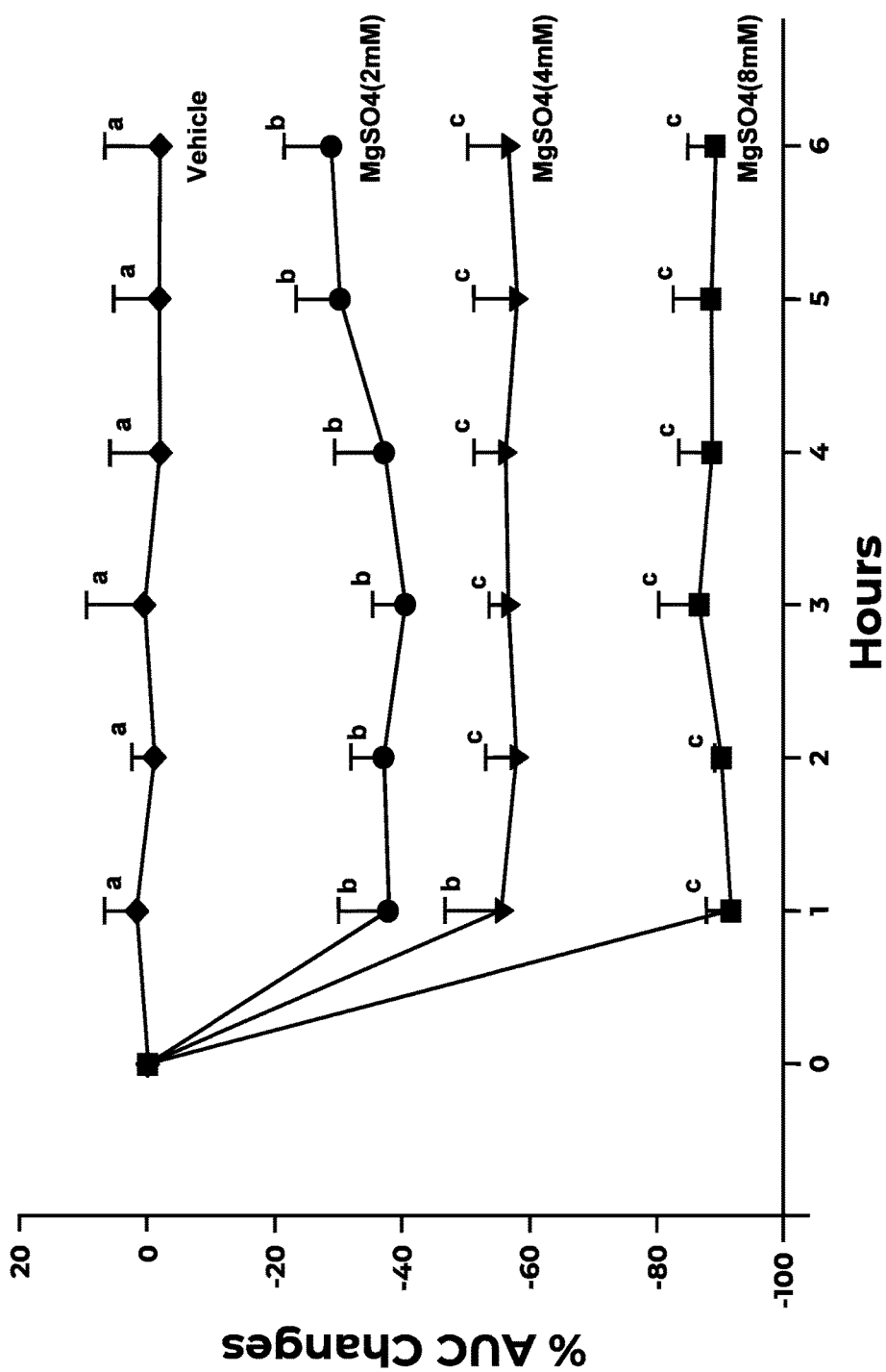
FIG. 10 depicts, in accordance with an embodiment herein, effects of various concentrations of $MgSO_4$ on myometrial contractility.

The inventors tested whether a soluble form of progesterone would inhibit human myometrial contractility in vitro and in vivo. The soluble form was equally effective in inhibiting myometrial contractility as compared to crystalline progesterone dissolved in ethanol (FIG. 9). In addition, the inventors showed that soluble progesterone inhibits uterine contractions (electromyographic activity) when given to pregnant rats in labor (FIGS. 8, 15, 16, 17). Recent studies with progesterone show promise in treatment of preterm labor but these preparations use crystalline progesterone which is usually given vaginally. Use of soluble progesterone offers many advantages as described above.

Figure 7:
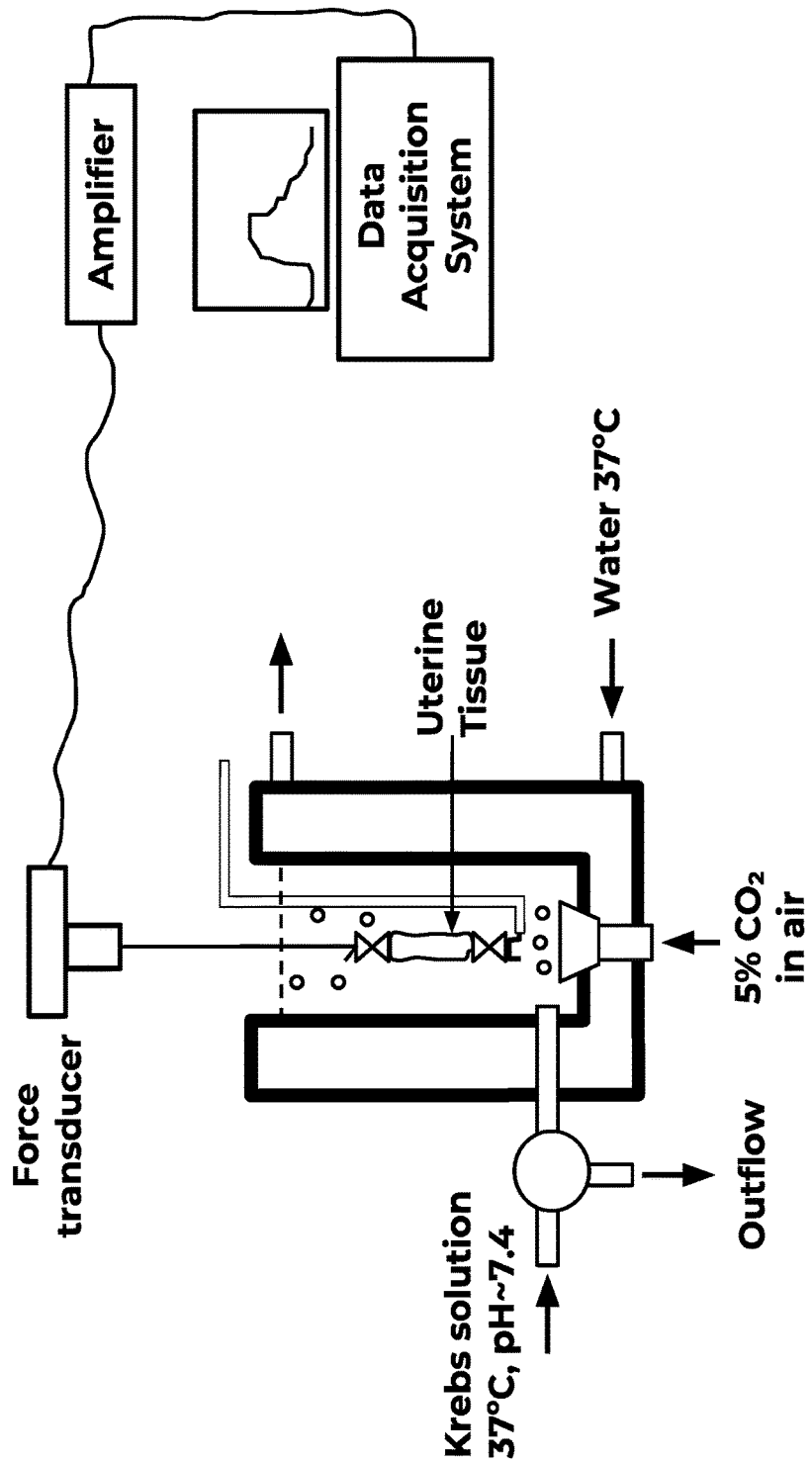
FIG. 7 depicts, in accordance with an embodiment herein, an organ chamber system set up for study of uterine contractions.
Figure 8:
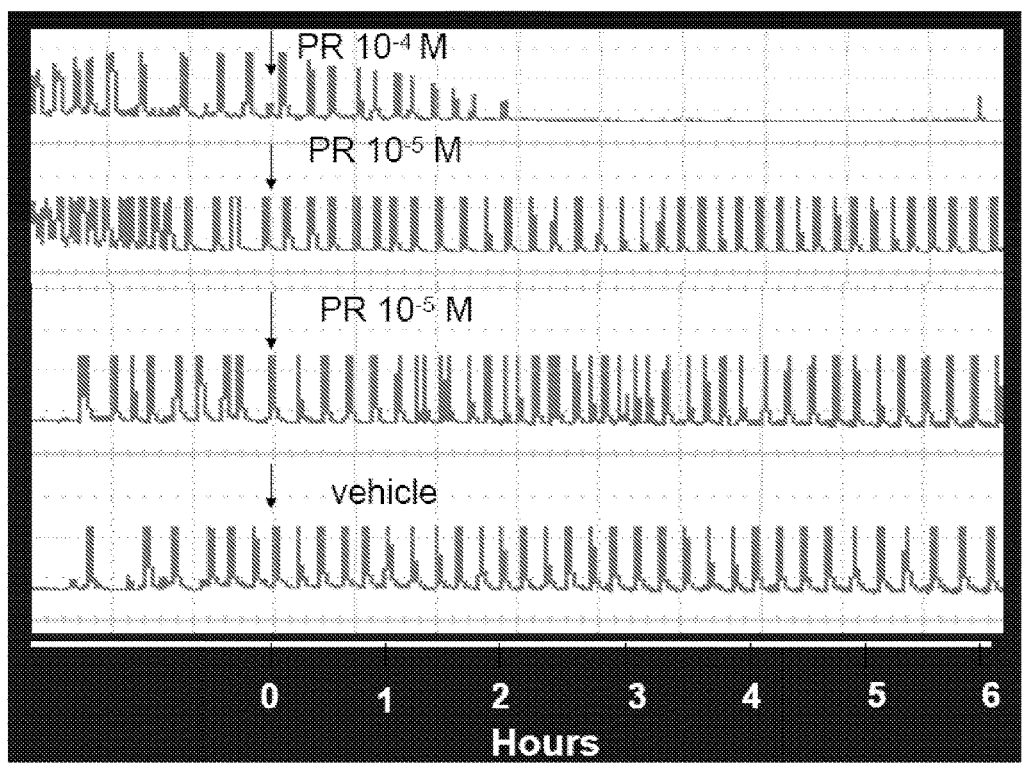
FIG. 8 depicts, in accordance with an embodiment herein, effects of progesterone (depicted as PR) on human myometrial contractions. As shown, $10^{-4}M$ progesterone inhibited myometrial contractions.

The inventors tested whether a soluble form of progesterone would inhibit human myometrial contractility in vitro (FIG. 7). FIG. 7 is a schematic drawing of the muscle bath that is used to measure uterine contractility in vitro. The system consists of a water jacketed chamber to maintain temperature at 37 degrees and an inner chamber where the tissue is suspended in Krebs'-Ringer solution and bubbled with air. The tissue is connected to a force transducer and the signals from the transducer are amplified, stored and analyzed by a data acquisition system.

Figure 11:
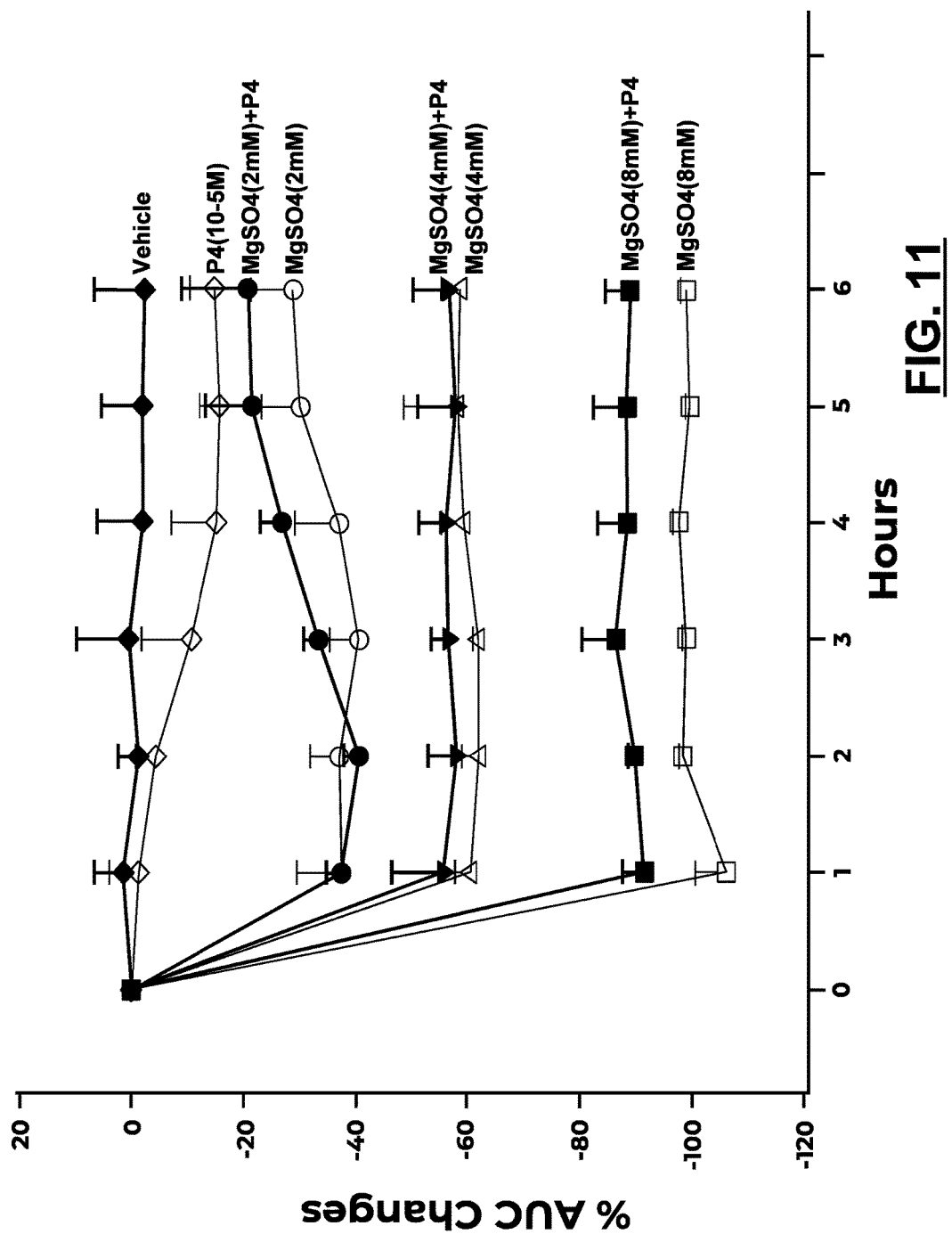
FIG. 11 depicts, in accordance with an embodiment herein, effects of progesterone (P4) with $MgSO_4$ on myometrial contractility.
Figure 12:
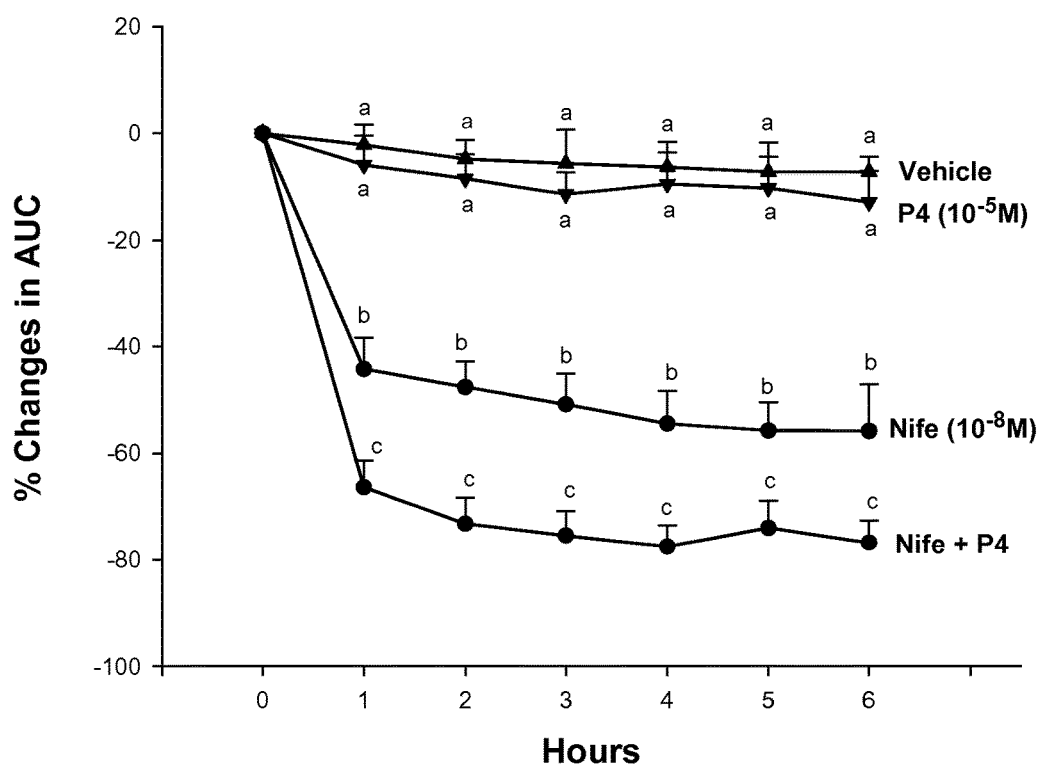
FIG. 12 depicts, in accordance with an embodiment herein, effects of nifedipine (Nife) and progesterone (P4) and their combination on myometrial contractility.
Figure 13:
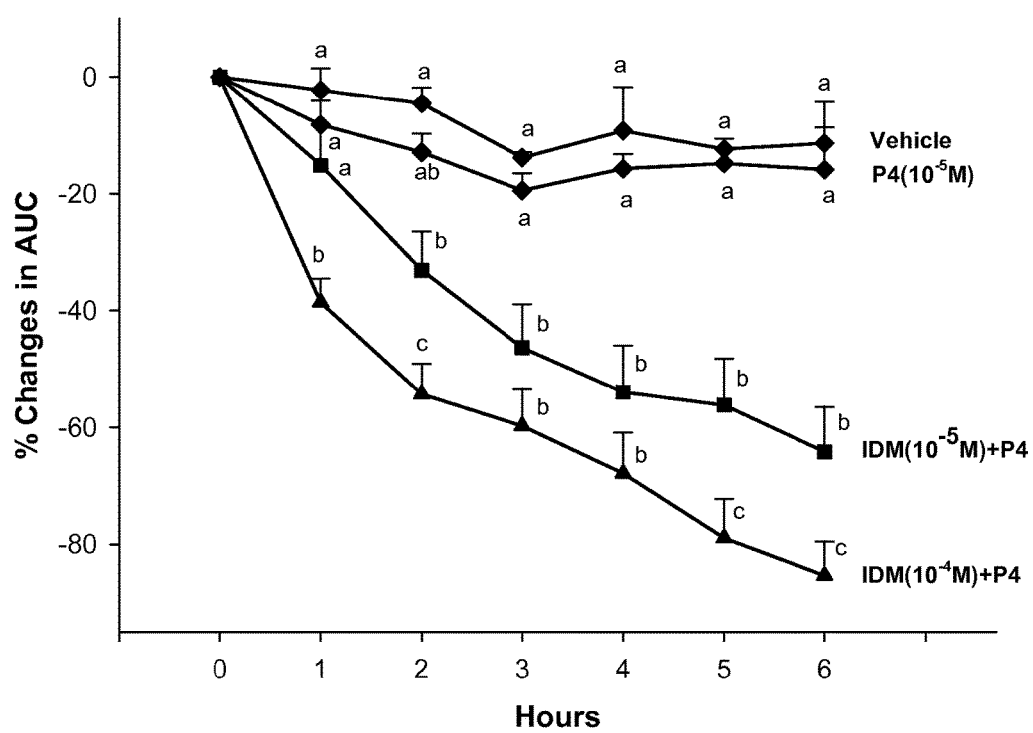
FIG. 13 depicts, in accordance with an embodiment herein, effects of indomethacin (IND) and progesterone (P4) and their combination on myometrial contractility.
Figure 14:
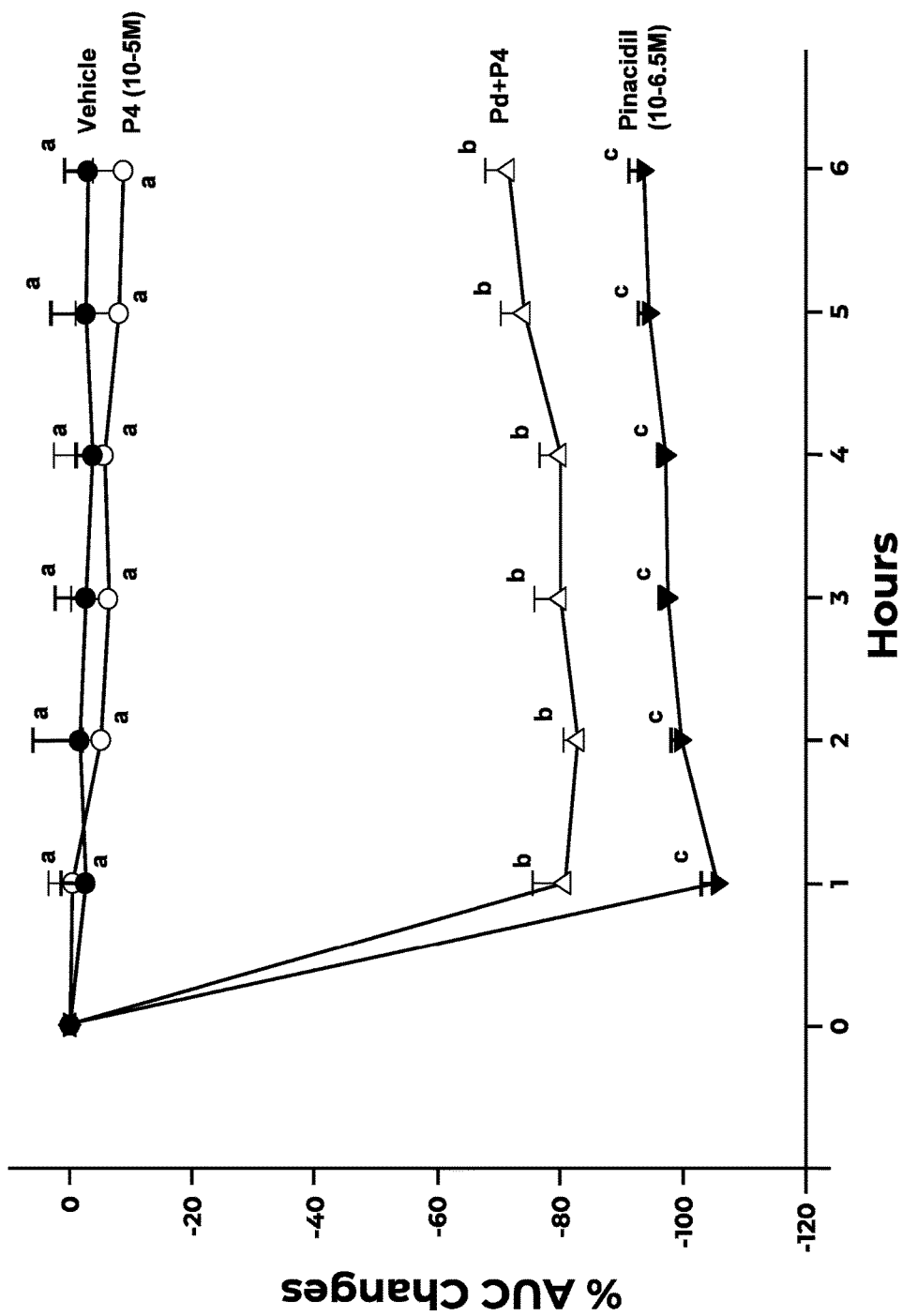
FIG. 14 depicts, in accordance with an embodiment herein, effect of pinacidil ($10^{-6.5}$M) alone, or with P4 ($10^{-5}$M) on human myometrium contractility (term, not in labor).

The soluble form of progesterone (P4) was found to be effective in inhibiting myometrial contractility (FIGS. 8, 15, 16 and 17). The inventors found that P4 inhibits myometrial contractility (soluble and crystalline in ETOH) (FIG. 9). Progesterone (P4) with nifedipine (Nife) (FIG. 11) or indomethacin (IND) (FIG. 12), but not $MgSO_4$ increased contractile inhibition, by additive or synergistic actions. Additionally, use of P4 with Nife or IND could also be useful for preterm labor treatment, and higher endogenous P4 levels can increase effectiveness of Nife or IND.

The inventors examined the direct effects of various tocolytics on uterine contractility with and without progesterone, as it was possible that a tocolytic used with progesterone would produce additive, synergistic or antagonistic action on contractility. Methods used for collecting samples and data were:
 IRB approval
 Informed consent
 Women at term not in labor (n=37 patients and 280 tissues)
 N=10/group (Based on power analysis)
 Cesarean section
 0.2×0.2×1.0 cm piece of tissue from lower uterine segment Samples used within 24 hours of collection Myometrial strips equilibrated with 1 gm of passive tension Spontaneous contractile activity stabilized P4 dissolved in ETOH added to tissue bath at 10-5 M concentration MgSO4, indomethacin, nifedipine and pinacidil dissolved in $H_2O$ or ethanol Solvent time-controls were run in parallel Contractile activity registered, stored and analyzed Statistics—One-way ANOVA used to determine statistical differences (P<0.05=significant).

The inventors found that P4 inhibits myometrial contractility (soluble and crystalline in ETOH). P4 with nifedipine (Nife) or indomethacin (IND), but not $MgSO_4$ increase contractile inhibition, by additive or synergistic actions. Additionally, use of P4 with Nife or IND could also be useful for PTL treatment, and higher endogenous P4 levels can increase effectiveness of Nife or IND. P4 decreases pinacidil inhibition of contractility possibly by interaction of agents at K+ channels.

As described herein, progesterone applied topically in many types of oils can inhibit delivery Soluble progesterone is usually applied in oil preparations because of its solubility. For example, by encapsulating progesterone in cyclodexrins progesterone becomes soluble and can be used parenterally, and by other routes of administration.

Figure 15:
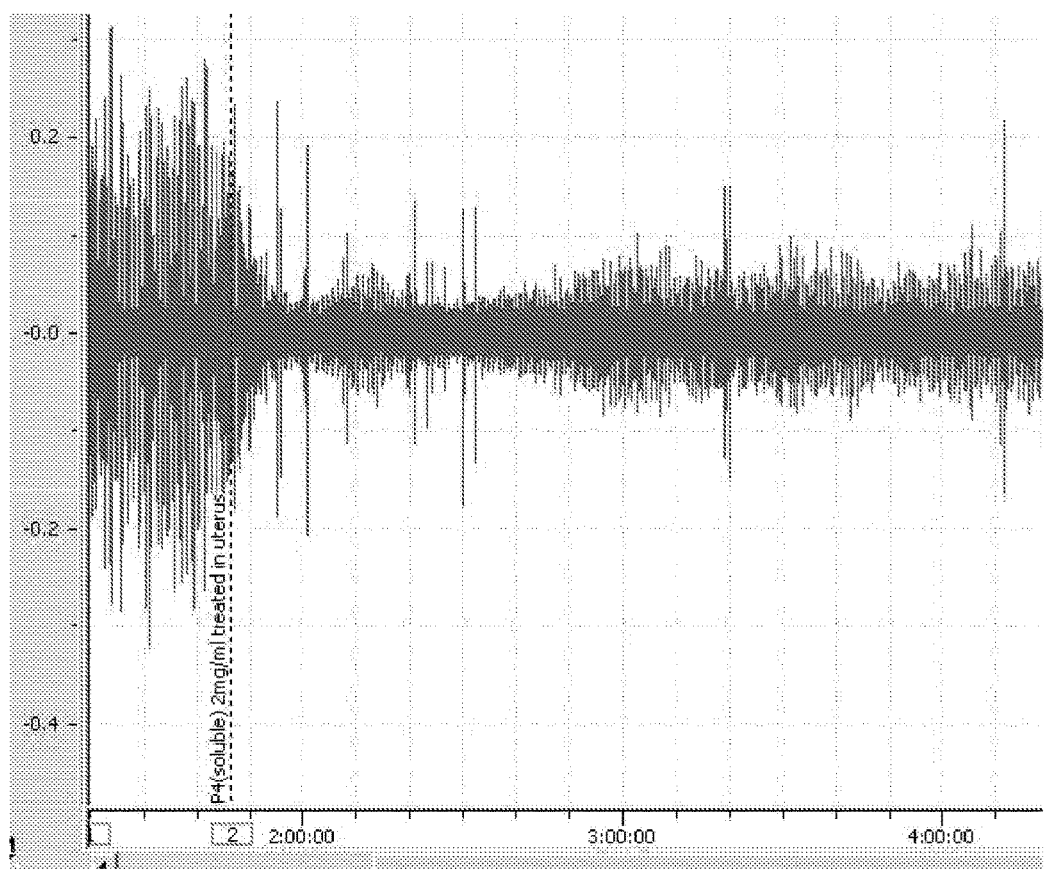
FIG. 15 depicts, in accordance with an embodiment herein, in vivo electromyographic activity of uterine contractility over one hour periods after treatment with soluble progesterone (P4) (dissolved in 0.9% NaCl) at 2 mg/ml marked in rats.

FIG. 15 depicts delay of delivery times in timed pregnant rats treated with progesterone (P4) with different routes and vehicles. Treatment was started on day 13 of gestation and continued until delivery of pups or until delivery was blocked at 80 hours (day 25) past day 22 of gestation. 8 am on day 22 is noted as hour 0 and delay is compared to control group treated only with vehicle. Treatment groups included: P4 in fish oil (vaginal, nasal, injection and topical groups), P4 in cocoa butter (rectal) and P4 in sesame oil (oral). All treatment groups received a total daily dose of 30 mg P4/day except the nasal and subcutaneous injection group which received 1 mg/day and 4 mg/day, respectively. Rectal, subcutaneous injection and topical administration in fish oil had significant delay of delivery.

Figure 16:
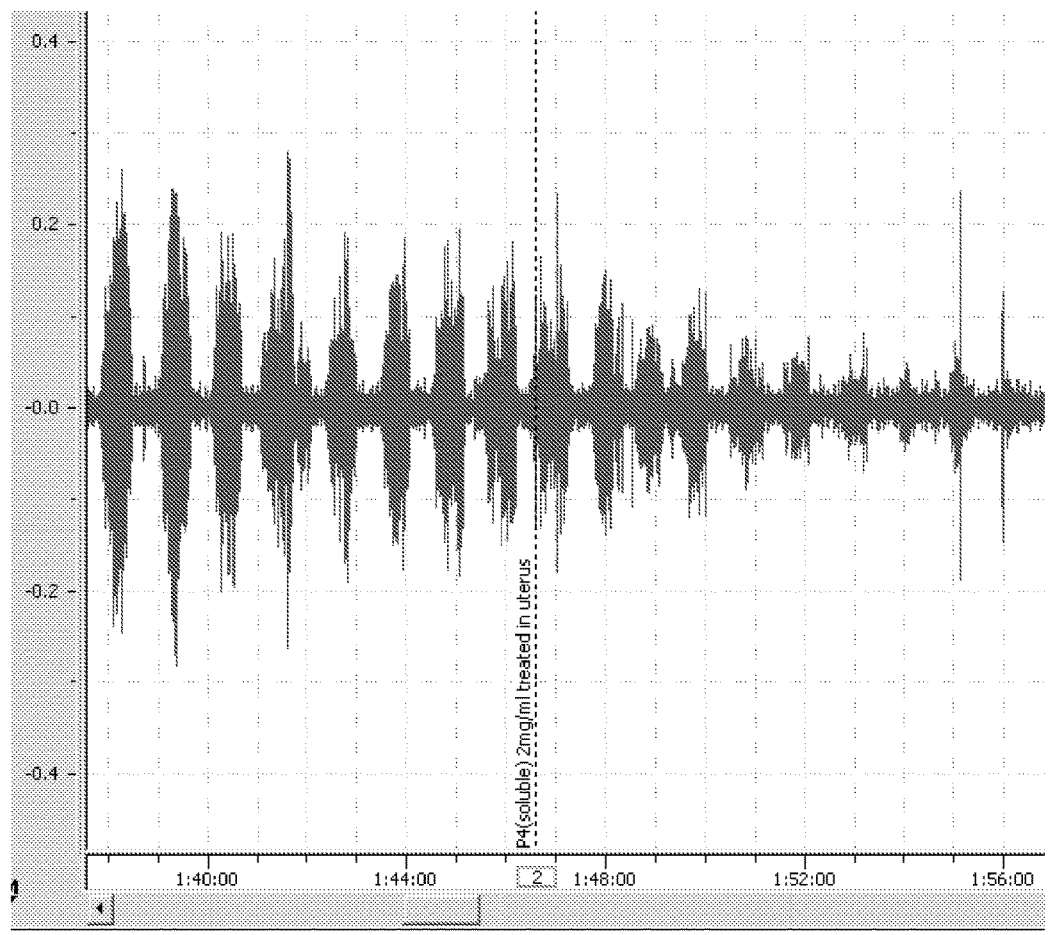
FIG. 16 depicts, in accordance with an embodiment herein, in vivo electromyographic activity of uterine contractility over four minute periods after treatment with soluble progesterone (P4) (dissolved in 0.9% NaCl) at 2 mg/ml marked in rats.

As depicted in FIG. 16, pregnant timed rats were treated topically with progesterone (P4) in different oil vehicles beginning on day 19 of gestation. Vehicles included: Omegasorb fish oil, coconut oil, corn oil and olive oil. Treatment was administered twice a day (15 mg P4, bid) and continued until delivery of pups or until complete block of delivery was observed. 8 am on day 22 is noted as hour 0 and complete block is determined by an 80 hour delay (day 25). All groups but corn oil had significant delay of delivery.

Figure 17:
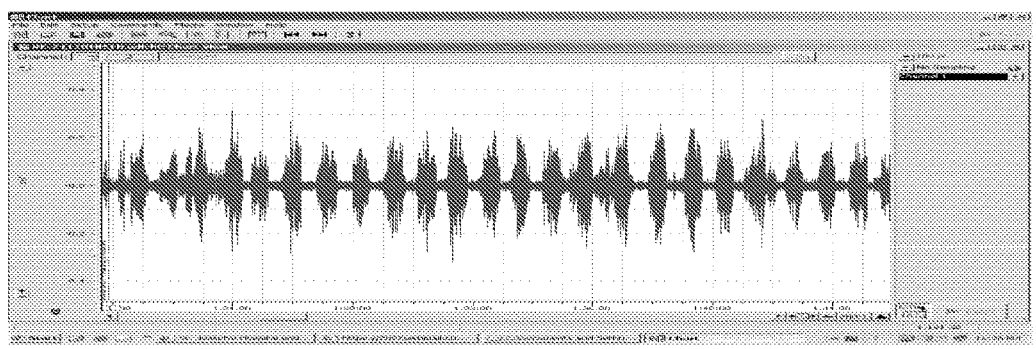
FIG. 17 depicts, in accordance with an embodiment herein, electromyographic activity of uterine contractility in rats both (A) before treatment, and (B) after treatment, with soluble progesterone (P4) (dissolved in 0.9% NaCl) at 2 mg/ml.
Figure 17:
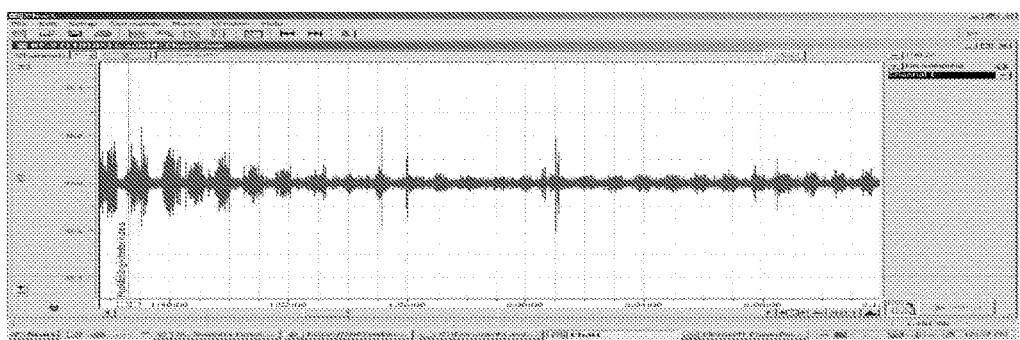

FIG. 17 depicts delay of delivery in time pregnant rats treated with progesterone (P4) with different vehicles. Treatment was started on day 20 of gestation and continued until delivery of pups or delivery was blocked at 80 hours (day 25). 8 am on day 22 is noted as hour 0 and delay is compared to control group treated only with vehicle. Treatment group included: DHA=Docosahexanoic acid, EPA=Eicosapentanoic acid (both omega-3 fatty acids), Nutraseafish oil, Nutrasea+D fish oil, GNC Triple Strength fish oil, Neptune Krill Oil, Omegasorb GNC fish oil. All treatment groups received a total daily dose of 30 mg P4. All treatment groups except EPA had significant delays when compared to controls but only Omegasorb GNC fish oil vehicle group demonstrated complete block of delivery.

Figure 18:
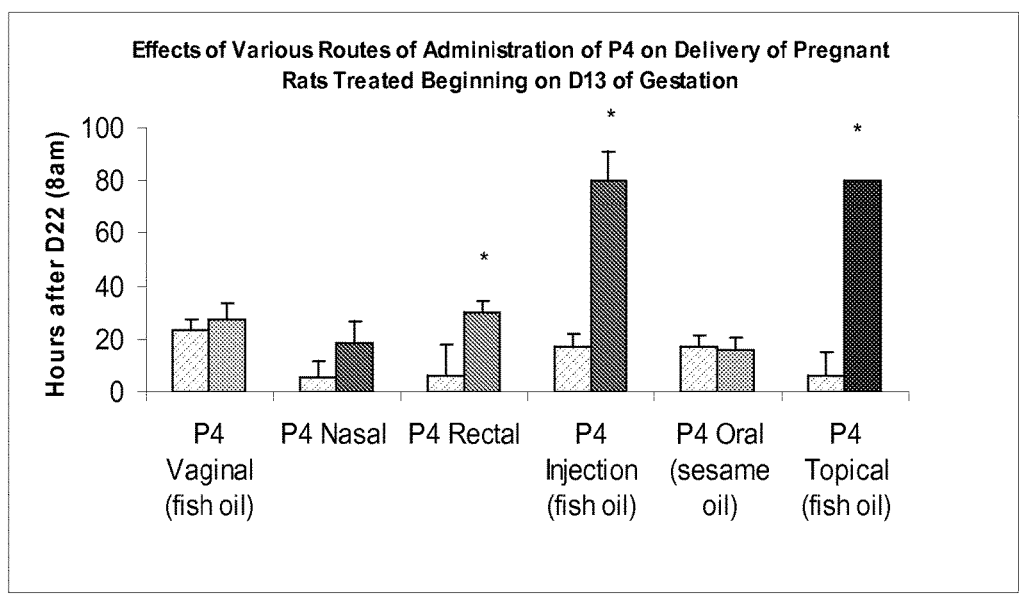
FIG. 18 depicts effects of various routes of administration of progesterone (P4) in delivery of pregnant rats treated beginning at day 13 (D13) of gestation.

FIG. 18 depicts delay of delivery in timed pregnant rats treated with progesterone (P4) with different vehicles. Treatment was started on day 20 of gestation and continued until delivery of pups or delivery was blocked at 80 hours (day 25). 8 am on day 22 is noted as hour 0 and delay is compared to control group treated only with vehicles. Vehicles included: ETOH=Ethanol, Mineral oil, Peppermint oil, Flaxseed oil, Vitamin E oil, Argan Oil, DMSO. All treatment groups received a total daily dose of 30 mg P4.

Figure 19:
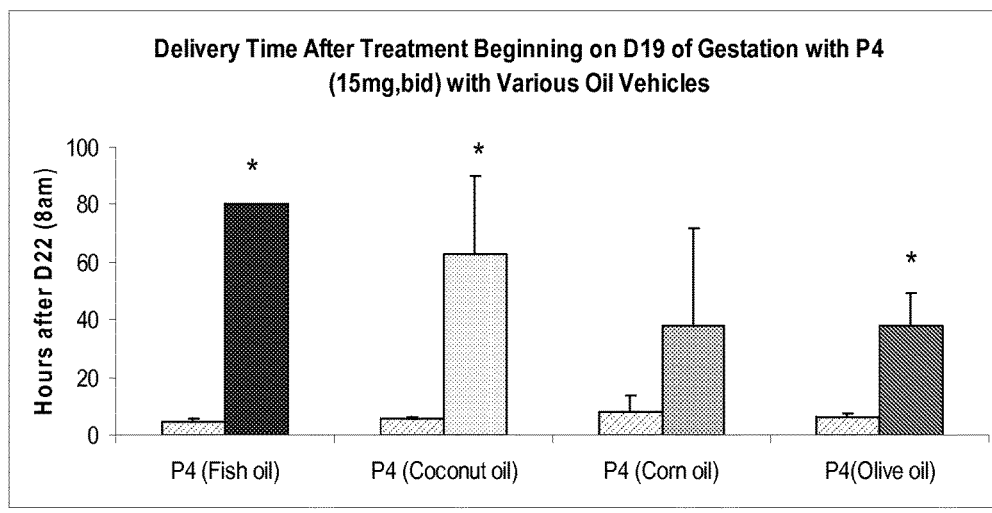
FIG. 19 depicts delivery time after treatment beginning at day 19 (D19) of gestation with progesterone (P4) with various oil vehicles.
Figure 20:
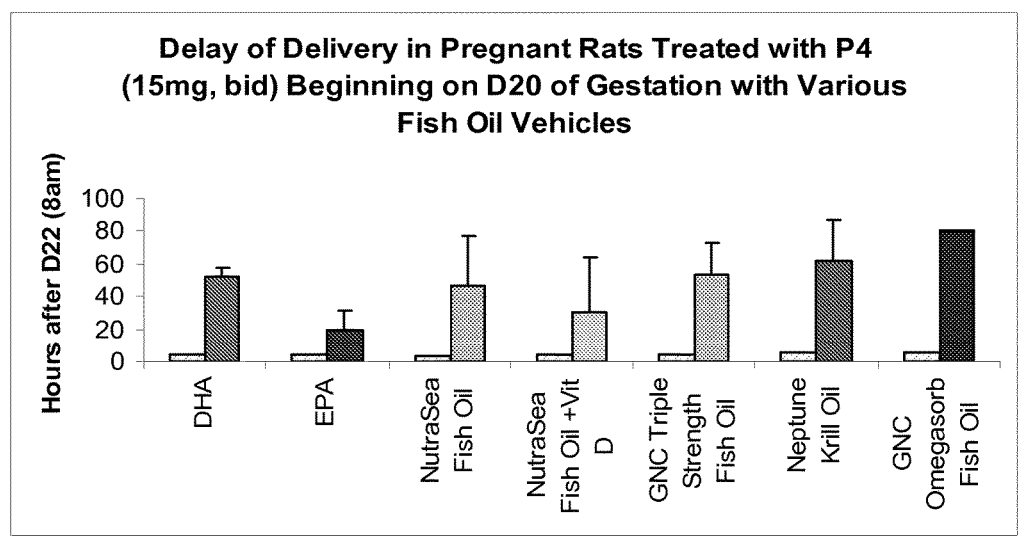
FIG. 20 depicts delay in pregnant rats treated with progesterone (P4) beginning at day 20 (D20) of gestation with various fish oil vehicles.
Figure 21:
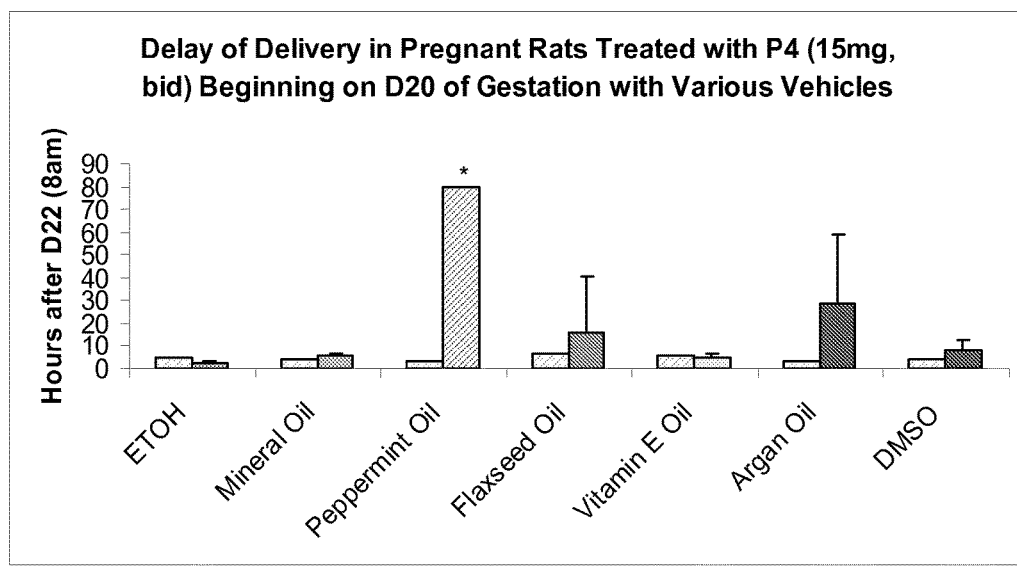
FIG. 21 depicts delay of delivery in pregnant rats treated with progesterone (P4) beginning at day 20 (D20) of gestation with various vehicles.
Figure 22:
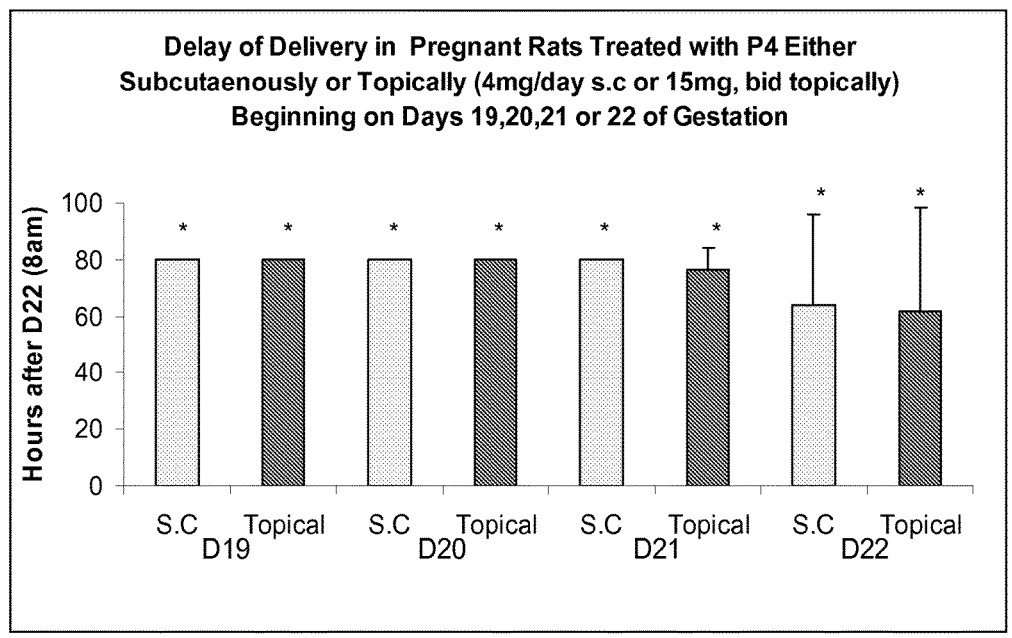
FIG. 22 depicts delay of delivery in pregnant rats treated with progesterone (P4) either subcutaneously or topically beginning at days 19, 20, 21 or 22 of gestation.
Figure 23:
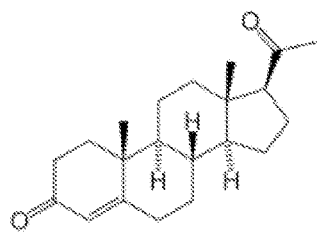
FIG. 23 depicts chemical structures of some embodiments of the invention.
Figure 23:
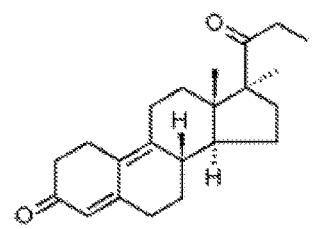
Figure 23:
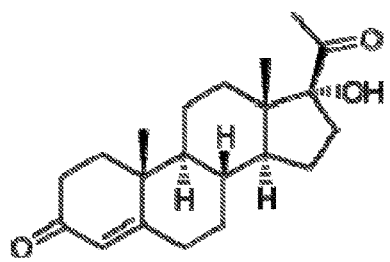
Figure 23:
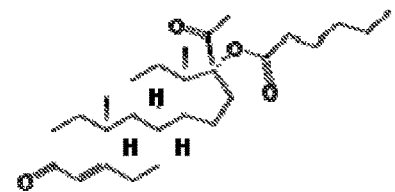
Figure 23:
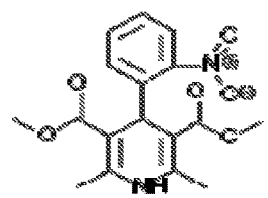
Figure 23:
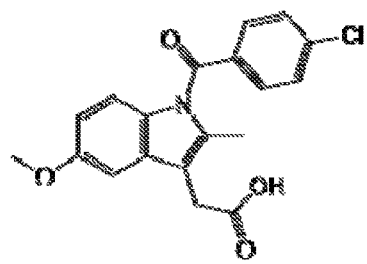

As depicted in FIG. 19, animals were treated either subcutaneously or topically with P4 in fish oil beginning on days 19, 20, 21 and 22 of gestation. Delivery time of timed pregnant rats treated with progesterone (P4) either with subcutaneous injection or topical application on different days of gestation. Treatment groups consisted of P4 in fish oil administered starting on different days of gestation and with different routes. Treatment was administered on either days 19, 20 21 or day 22 of gestation and continued until delivery of pups or until complete block of delivery was observed. 8 am on day 22 is noted as Hour 0 and complete block is determined by an 80 hour delay (day 25). All groups had significant delay of delivery. D19 topical application and D21 subcutaneous injection demonstrated complete block in all animals. Delivery was blocked or significantly delayed even when treatment was begun just prior to delivery on day 22.

Figure 6:
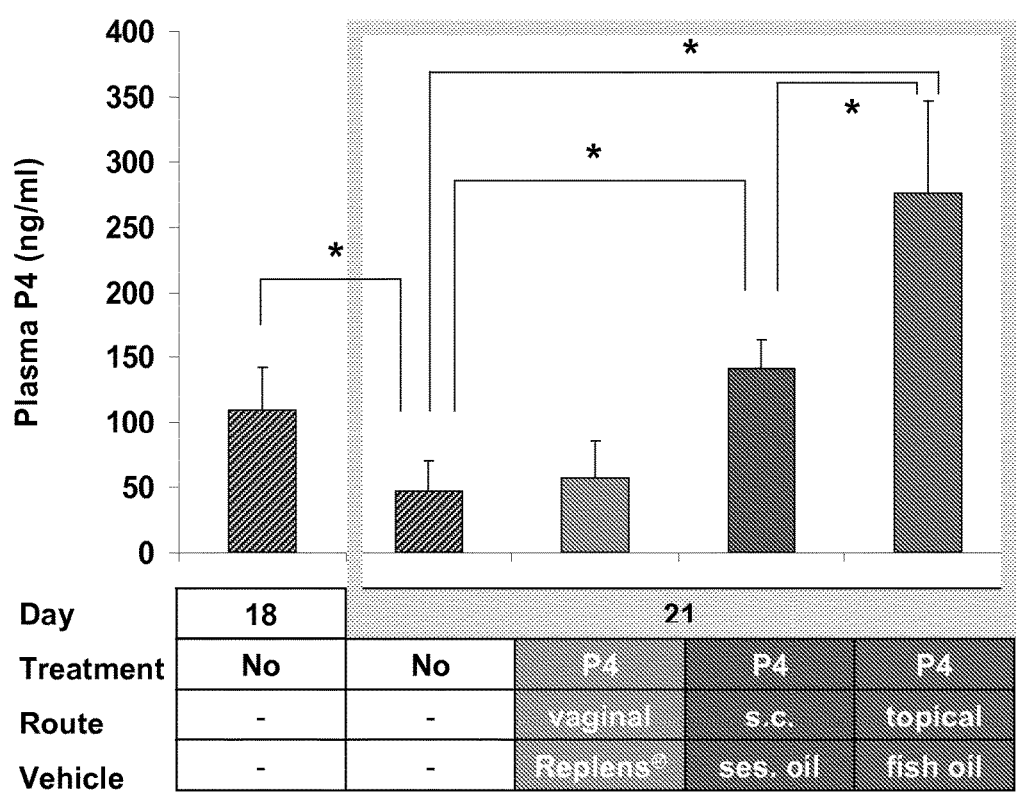
FIG. 6 depicts plasma levels of progesterone following various treatments. Plasma progesterone (P4) levels in pregnant rats at day 18 and 21 days of gestation after treatment with P4 vaginal gel (15 mg bid), P4 injections (4 mg subcutaneous daily), topical P4 in fish oil (15 mg bid) and controls (Ctr) treated with vehicles.
Figure 24:
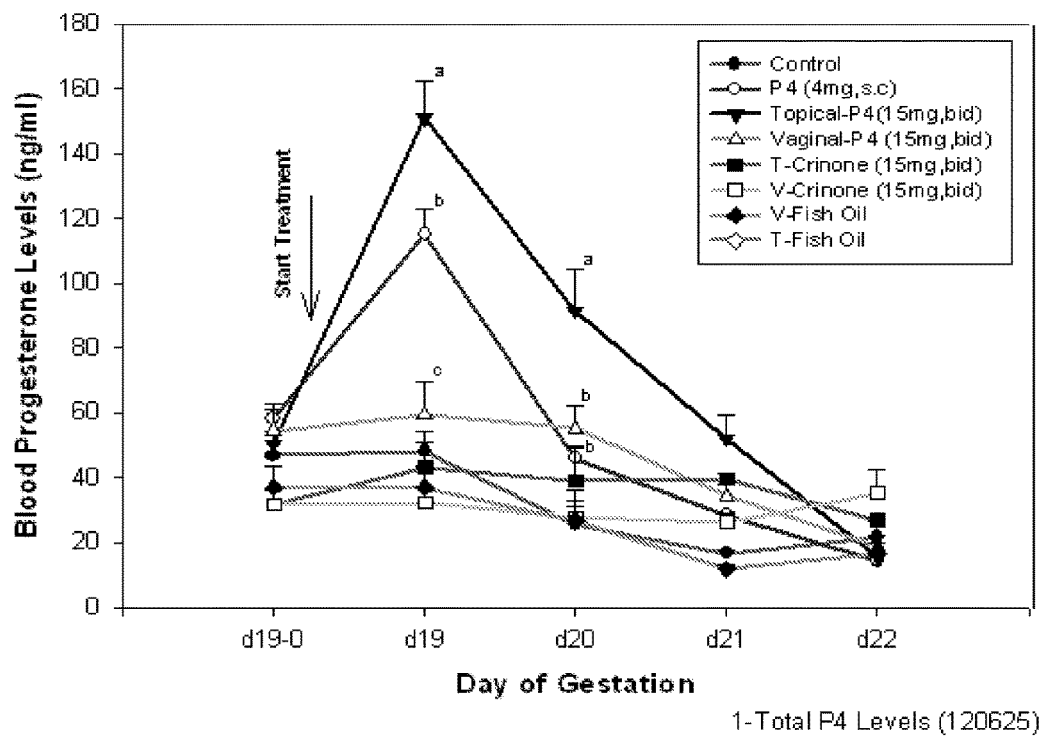
FIG. 24 depicts pharmokinetic data related to plasma serum levels after topical delivery in rats following various treatments on day 19 of gestation (single treatment only).

As depicted in FIG. 6, topical administration of progesterone is highly effective in increasing plasma circulation levels of progesterone, when compared to vaginal or subcutaneous injection, when provided at day 21. As depicted in FIG. 24, plasma levels increase markedly after only a single treatment only day 19, proving to be even higher than subcutaneous injection, and can persist for 1, 2, or more days following administration.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources and composition of progestogens, including progesterone, further including pharmaceutical compositions, preparation methods, dosages, administration methods, and/or other diseases and conditions and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of inhibiting preterm birth in a subject in need thereof, comprising: (i) providing a composition comprising progesterone (P4) or a salt thereof, in an oil selected from the group consisting of sesame oil, fish oil, corn oil, olive oil, coconut oil, krill oil, peppermint oil, and argan oil; and (ii) topically administering a therapeutically effective amount of the composition to the subject: wherein the therapeutically effective amount of the composition is topically administered to an abdominal surface or back of the subject; and wherein the effective amount of the steroid hormone is about 25 mg/day to 35 mg/day; thereby inhibiting preterm birth.

2. A method for preventing preterm birth in a subject in need thereof by the method of claim 1.

3. The method of claim 1, wherein the oil is fish oil.

4. The method of claim 1, wherein the effective amount of the oil is about 0.05-0.1 ml/mg of steroid hormone, 0.1-0.2 ml/mg of steroid hormone, 0.2-0.3 ml/mg of steroid hormone, 0.3-0.4 ml/mg of steroid hormone, 0.4-0.5 ml/mg of steroid hormone, 0.5-0.6 ml/mg of steroid hormone, 0.6-0.7 ml/mg of steroid hormone, 0.7-0.8 ml/mg of steroid hormone, 0.8-0.9 ml/mg of steroid hormone, 0.9-1.0 ml/mg of steroid hormone, 1.0-5.0 ml/mg of steroid hormone, 5.0-10.0 ml/mg of steroid hormone, 10.0-15.0 ml/mg of steroid hormone, 15.0-20.0 ml/mg of steroid hormone, 20.0-25.0 ml/mg of steroid hormone or 25.0-30.0 ml/mg of steroid hormone.

5. The method of claim 1, wherein the composition is administered beginning at about $18^{th}$ to about $22^{nd}$ week of gestation and ending at about $37^{th}$ week of gestation.

6. The method of claim 1, wherein the composition is administered beginning at about $16^{th}$ week of gestation and ending at about $37^{th}$ week of gestation.

7. The method of claim 1, wherein the composition is administered beginning at the time of positive pregnancy until the $37^{th}$ week of gestation or from time preterm labor is suspected to a time when delivery is imminent.

8. The method of claim 1, wherein the composition is administered for about 2 to 4 weeks, for about 4 to 6 weeks, for about 6 to 8 weeks, for about 8 to 10 weeks, for about 10 to 12 weeks, for about 12 to 14 weeks or for about 14 to 19 weeks.

9. The method of claim 1, wherein the composition is administered for about 20 weeks, for about 21 weeks, for about 22 weeks, for about 23 weeks, for about 25 weeks, for about 26 weeks, for about 27 weeks, for about 28 weeks or for about 29 weeks.

10. The method of claim 1, wherein the composition is in a soluble form or a gel form.

11. The method of claim 1, further comprising administering to the subject an effective amount of nifedipine or indomethacin.

12. The method of claim 1, wherein the subject is selected from the group consisting of human, monkey, ape, dog, cat, cow, horse, rabbit, mouse, pig and rat.

13. The method of claim 12, wherein the subject is human.

* * * * *